United States Patent
Mistretta et al.

(10) Patent No.: US 11,406,339 B2
(45) Date of Patent: Aug. 9, 2022

(54) SYSTEM AND METHOD FOR DETERMINING VASCULAR VELOCITY USING MEDICAL IMAGING

(71) Applicant: Wisconsin Alumni Research Foundation, Madison, WI (US)

(72) Inventors: Charles A. Mistretta, Middleton, WI (US); Martin Wagner, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 354 days.

(21) Appl. No.: 16/685,713

(22) Filed: Nov. 15, 2019

(65) Prior Publication Data

US 2020/0155103 A1 May 21, 2020

Related U.S. Application Data

(60) Provisional application No. 62/768,350, filed on Nov. 16, 2018.

(51) Int. Cl.
*A61B 6/00* (2006.01)
*A61B 5/021* (2006.01)
(Continued)

(52) U.S. Cl.
CPC .............. *A61B 6/507* (2013.01); *A61B 5/021* (2013.01); *A61B 5/026* (2013.01); *A61B 5/4884* (2013.01);
(Continued)

(58) Field of Classification Search
None
See application file for complete search history.

(56) References Cited

U.S. PATENT DOCUMENTS

| | | | |
|---|---|---|---|
| 7,545,901 B2 | 6/2009 | Mistretta |
| 7,991,452 B2 | 8/2011 | Mistretta |
| 8,643,642 B2 | 2/2014 | Mistretta |
| 10,368,818 B2 | 8/2019 | Mistretta |

(Continued)

OTHER PUBLICATIONS

Davis, B., et al. "4D digital subtraction angiography: implementation and demonstration of feasibility." American Journal of Neuroradiology 34.10 (2013): 1914-1921.

(Continued)

*Primary Examiner* — Hoon K Song
(74) *Attorney, Agent, or Firm* — Quarles & Brady LLP

(57) ABSTRACT

A system and method are provided for determining vascular velocity using non-invasively acquired medical images. The method includes reconstructing CT angiography (CTA) data into a plurality of images of the subject by producing a composite image using the CTA data corresponding to a set of the plurality of view angles, backprojecting each view angle in the CTA data and weighting a value backprojected into at image pixel by an attenuation value of a corresponding pixel in the composite image, and summing backprojected values for each image pixel to produce a CT image of the subject. The method also includes determining a flow direction or a velocity of flow within a vessel, calculating, using the flow direction or velocity, a pressure in the vessel, and generating a quantitative map of the subject indicating the flow direction, velocity, or pressure in the vessel against an image of the subject including the vessel.

14 Claims, 18 Drawing Sheets

(51) Int. Cl.
    *A61B 5/026*     (2006.01)
    *A61B 5/00*     (2006.01)
    *G06T 11/00*     (2006.01)
    *G06T 7/20*     (2017.01)
    *G06T 7/00*     (2017.01)
    *A61B 6/03*     (2006.01)

(52) U.S. Cl.
CPC .............. *A61B 6/032* (2013.01); *A61B 6/504* (2013.01); *A61B 6/5217* (2013.01); *A61B 6/5235* (2013.01); *G06T 7/0014* (2013.01); *G06T 7/20* (2013.01); *G06T 11/006* (2013.01); *G06T 2207/10081* (2013.01); *G06T 2207/30104* (2013.01); *G06T 2210/41* (2013.01); *G06T 2211/404* (2013.01); *G06T 2211/421* (2013.01)

(56) References Cited

U.S. PATENT DOCUMENTS

| | | | | |
|---|---|---|---|---|
| 2014/0313196 | A1* | 10/2014 | Mistretta | G06T 11/008 345/424 |
| 2015/0119705 | A1* | 4/2015 | Tochterman | A61B 6/504 600/431 |
| 2018/0144475 | A1* | 5/2018 | Hoi | A61B 6/504 |
| 2019/0209114 | A1* | 7/2019 | Nishioka | A61B 6/032 |

OTHER PUBLICATIONS

Garcia, D., et al. "Assessment of aortic valve stenosis severity: a new index based on the energy loss concept." Circulation 101.7 (2000): 765-771.

Mistretta, C. A. "Sub-Nyquist acquisition and constrained reconstruction in time resolved angiography." Medical physics 38.6Part1 (2011): 2975-2985.

Mistretta, C. A. "The Development of modern Time-Resolved angiographic imaging; applications of under sampled acquisition and constrained reconstruction." Medical Physics International Journal 1.1 (2013).

Mistretta, C. A. "Undersampled radial MR acquisition and highly constrained back projection (HYPR) reconstruction: Potential medical imaging applications in the post-Nyquist era." Journal of Magnetic Resonance Imaging: An Official Journal of the International Society for Magnetic Resonance in Medicine 29.3 (2009): 501-516.

Mistretta, C. A., et al. "Highly constrained backprojection for time-resolved MRI." Magnetic Resonance in Medicine: An Official Journal of the International Society for Magnetic Resonance in Medicine 55.1 (2006): 30-40.

Taqueti, V. R., et al. "Excess cardiovascular risk in women relative to men referred for coronary angiography is associated with severely impaired coronary flow reserve, not obstructive disease." Circulation 135.6 (2017): 566-577.

Wu, Y., et al. "Fast whole-brain 4D contrast-enhanced MR angiography with velocity encoding using undersampled radial acquisition and highly constrained projection reconstruction: image-quality assessment in volunteer subjects." American Journal of Neuroradiology 32.3 (2011): E47-E50.

Wu, Y., et al. "CE-MRA of the lower extremities using HYPR stack-of-stars." Journal of Magnetic Resonance Imaging: An Official Journal of the International Society for Magnetic Resonance in Medicine 29.4 (2009): 917-923.

Xaplanteris, P., et al. "Five-year outcomes with PCI guided by fractional flow reserve." New England Journal of Medicine 379.3 (2018): 250-259.

* cited by examiner $p_1$ FIG. 9C $p_2$

SYSTEM AND METHOD FOR DETERMINING VASCULAR VELOCITY USING MEDICAL IMAGING

CROSS-REFERENCE TO RELATED APPLICATIONS

The present application is based on, claims priority to, and incorporates herein by reference in its entirety for all purposes, U.S. Provisional Application Ser. No. 62/768,350, filed Nov. 16, 2018, and entitled, "SYSTEMS AND METHODS FOR DETERMINING VASCULAR VELOCITY."

BACKGROUND

The present disclosure is related to angiography and, in particular, the disclosure relates to a system and method for determining vascular velocity using angiographic images and techniques.

In a computed tomography system, an x-ray source projects a fan-shaped beam which is collimated to lie within an X-Y plane of a Cartesian coordinate system, termed the "image plane." The x-ray beam passes through the object being imaged, such as a medical patient, and impinges upon an array of radiation detectors. The intensity of the transmitted radiation is dependent upon the attenuation of the x-ray beam by the object and each detector produces a separate electrical signal that is a measurement of the beam attenuation. The attenuation measurements from all the detectors are acquired separately to produce what is called the "transmission profile," or "attenuation profile" or "projection."

The source and detector array in a conventional CT system are rotated on a gantry within the imaging plane and around the object so that the angle at which the x-ray beam intersects the object constantly changes. The transmission profile from the detector array at a given angle is referred to as a "view" and a "scan" of the object comprises a set of views made at different angular orientations during one revolution of the x-ray source and detector. In a 2D scan, data is processed to construct an image that corresponds to a two dimensional slice taken through the object. The prevailing method for reconstructing an image from 2D data is referred to in the art as the filtered backprojection technique. This image reconstruction process converts the attenuation measurements acquired during a scan into integers called "CT numbers" or "Hounsfield units", which are used to control the brightness of a corresponding pixel on a display.

The filtered backprojection image reconstruction method is the most common technique used to reconstruct CT images from acquired transmission profiles. As shown in FIG. 1A each acquired x-ray transmission profile 100 is backprojected onto the field of view (FOV) 102 by projecting each ray sum 104 in the profile 100 through the FOV 102 along the same ray path that produced the ray sum 104 as indicated by arrows 106. In projecting each ray sum 104 in the FOV 102 we have no a priori knowledge of the subject and the assumption is made that the x-ray attenuation in the FOV 102 is homogeneous and that the ray sum should be distributed equally in each pixel through which the ray path passes. For example, a ray path 108 is illustrated in FIG. 1A for a single ray sum 104 in one transmission profile 100 and it passes through N pixels in the FOV 102. The attenuation value (P) of this ray sum 104 is divided up equally between these N pixels:

$$\mu_n = (P \times 1)/N \quad (1);$$

where: $\mu_n$ is the attenuation value distributed to the $n^{th}$ pixel in a ray path having N pixels.

Clearly, the assumption that attenuation in the FOV 102 is homogeneous is not correct. However, as is well known in the art, if certain corrections are made to each transmission profile 100 and a sufficient number of profiles are acquired at a corresponding number of projection angles, the errors caused by this faulty assumption are minimized and image artifacts are suppressed. In a typical filtered backprojection method of image reconstruction, anywhere from 400 to 1000 views are typically required to adequately suppress image artifacts in a 2D CT image.

There are a number of clinical applications where the time required to acquire a large number of views is not available. In time-resolved angiography, for example, a series of images are acquired as contrast agent flows into the region of interest. Each image is acquired as rapidly as possible to obtain a series of snapshots that depicts the in-flow of contrast. This application is particularly challenging when imaging coronary arteries or other vessels that require cardiac gating to suppress motion artifacts.

CT angiography (CTA) is a CT imaging application that produces detailed CT projection images of both blood vessels and tissues in an anatomical body. A contrast agent, such as an iodine-rich dye, can be injected in a vessel to increase the contrast of blood vessels, for example, compared to soft tissues. A plurality of CT projection images are acquired while, or after, the contrast agent moves into the vessels within an anatomical region of interest. The acquisition of a sequence of CT projection images can allow for tracking of the movement of the contrast agent into blood vessels within the imaged anatomical region.

Fractional flow reserve (FFR) is routinely measured invasively in the catheterization laboratory and has proved to be useful in identifying patients that should be treated with intravascular procedures (Xaplanteris et al., N. Engl. J. Med., 2018; 379:250-259). There is currently great interest in using the purely anatomical information provided by coronary CTA to derive model-dependent quantitative information, particularly FFR. Some have sought to calculate FFR non-invasively (i.e., image-based FFR or CT FFR) using computational fluid dynamics and, more recently, has been calculated with deep learning algorithms. Attempts to calculate FFR non-invasively have correlated reasonably well with invasively-calculated FFR, except for intermediate values of FFR. That is, non-invasively calculated values of FFR that are outside the extremes have been shown to correlate poorly with actual measurements, such as described Di Carli, Circulation, 2017 135(6):566-77. As such, clinical utility of non-invasive FFR calculations is limited or questionable. Further complicating the utility of non-invasively calculated or "image-derived" FFR using computational fluid dynamics (CFD) analysis is that the results are not available for several hours as the calculations are performed.

These shortcomings of current methods for deriving FFR frustrate the clinical needs. For example, it is known that FFR is not sensitive to the effects of microvascular disease and provides false negatives in these patients (Di Carli, supra). This is important for patients with diabetes. As such, some have tried to use others measures, such as coronary flow reserve (CFR), which is sensitive to both epicardial disease and microvascular disease (Di Carli, supra) but does not enable the valuation of these effects separately. Furthermore, CFR is not derived using the CFD or deep learning algorithms.

Therefore, it would be desirable to have systems and methods that improves the available information related to angiography images, such as by providing flow or velocity information or other quantitative information.

SUMMARY

In accordance with one aspect of the present disclosure, a method is provided for determining vascular velocity using non-invasively acquired medical images. The method includes receiving, at a computer, computed tomography angiography (CTA) data acquired from a subject using a plurality of view angles. The method also includes reconstructing, using the computer, the CTA data into a plurality of images of the subject by producing a composite image using the CTA data corresponding to a set of the plurality of view angles, backprojecting each view angle in the CTA data and weighting a value backprojected into at image pixel by an attenuation value of a corresponding pixel in the composite image, and summing backprojected values for each image pixel to produce a CT image of the subject. The method further includes determining, using the computer, at least one of a flow direction or a velocity of flow within a vessel in the plurality of images of the subject and calculating, using the computer and the at least one of flow direction or velocity, a pressure in the vessel. The method also includes generating, using the computer, a quantitative map of the subject indicating at least one of flow direction, velocity, or pressure in the vessel against an image of the subject including the vessel.

In accordance with another aspect of the present disclosure, a system is provided for generating quantitative computed tomography (CT) angiographic images. The system includes a rotatable gantry including a radiation source and a detector coupled thereto, wherein the rotatable gantry is configured to receive a subject to rotate the radiation source and the detector around the subject to acquire a set of projection views forming CTA data of the subject. The system also includes a computer system programmed to receive the CTA data from the detector and generate quantitative CTAs by producing a composite image using the CTA data corresponding to a set of the plurality of view angles, backprojecting each view angle in the CTA data and weighting a value backprojected into at image pixel by an attenuation value of a corresponding pixel in the composite image, and summing backprojected values for each image pixel to produce a CT image of the subject. The computer is further programmed to determine at least one of a flow direction or a velocity of flow within a vessel in the plurality of images of the subject, calculate, using the at least one of flow direction or velocity, a pressure in the vessel, and generate a quantitative map of the subject indicating at least one of flow direction, velocity, or pressure in the vessel against an image of the subject including the vessel. The system also includes a display configured to display the quantitative map of the subject against the image of the subject including the vessel.

Various other features of the present invention will be made apparent from the following detailed description and the drawings.

BRIEF DESCRIPTION OF THE DRAWINGS

FIG. 9C is an illustration of the vessel of FIG. 9B showing the position of two calculation points for summing contrast medium.

DETAILED DESCRIPTION

Non-invasive, image derived information is invaluable to modern clinical medicine. Even the advent of highly-efficient technologies, such highly constrained projection reconstruction (HYPR) techniques applied to CT, such as described in U.S. Pat. No. 7,545,901, and 4D DSA, such as described in U.S. Pat. No. 8,643,642, alone do not provide clinicians with quantitative angiographic information.

Figure 1A:
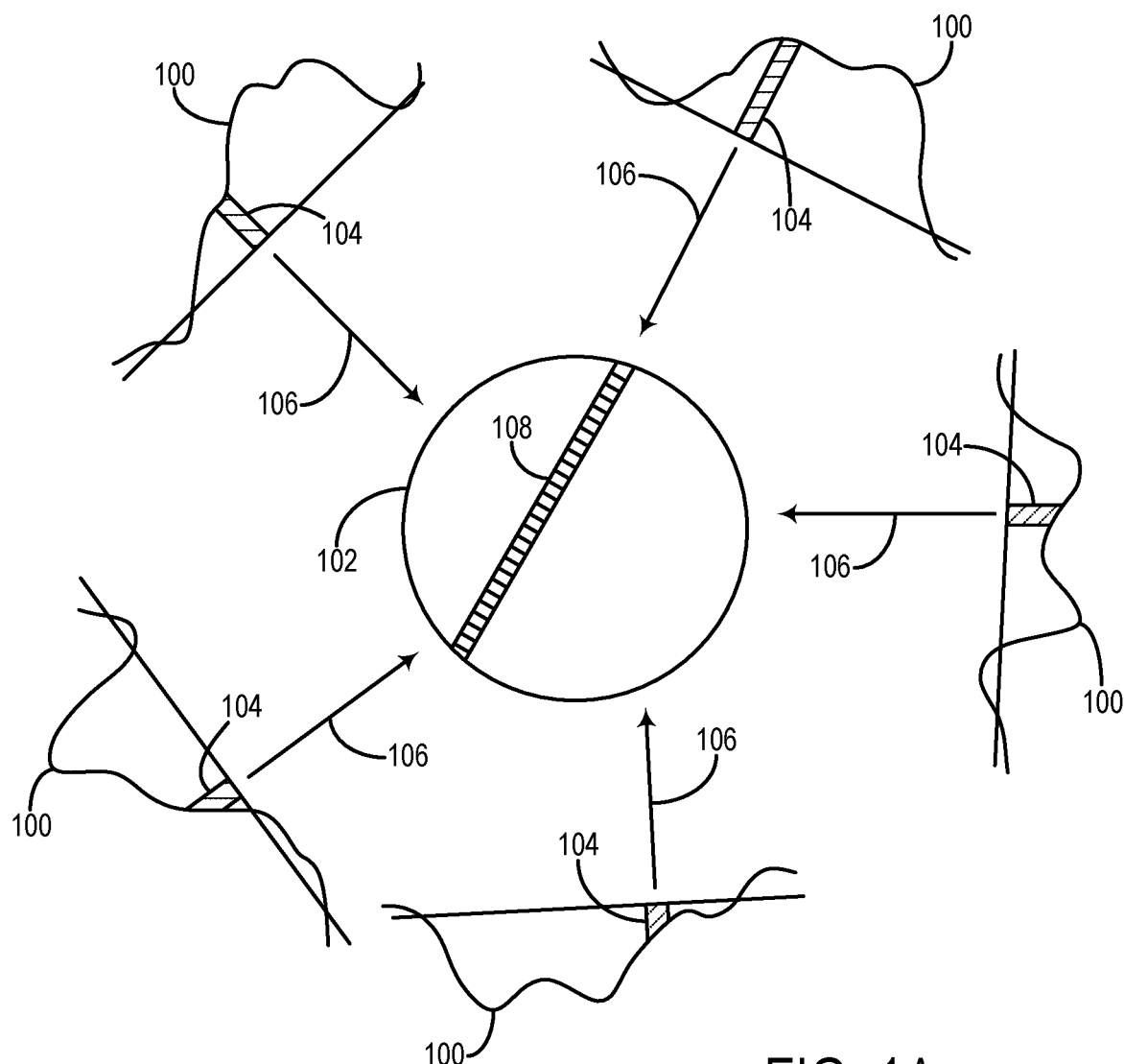
FIG. 1A is a pictorial representation of a conventional backprojection image reconstruction method.
Figure 1B:
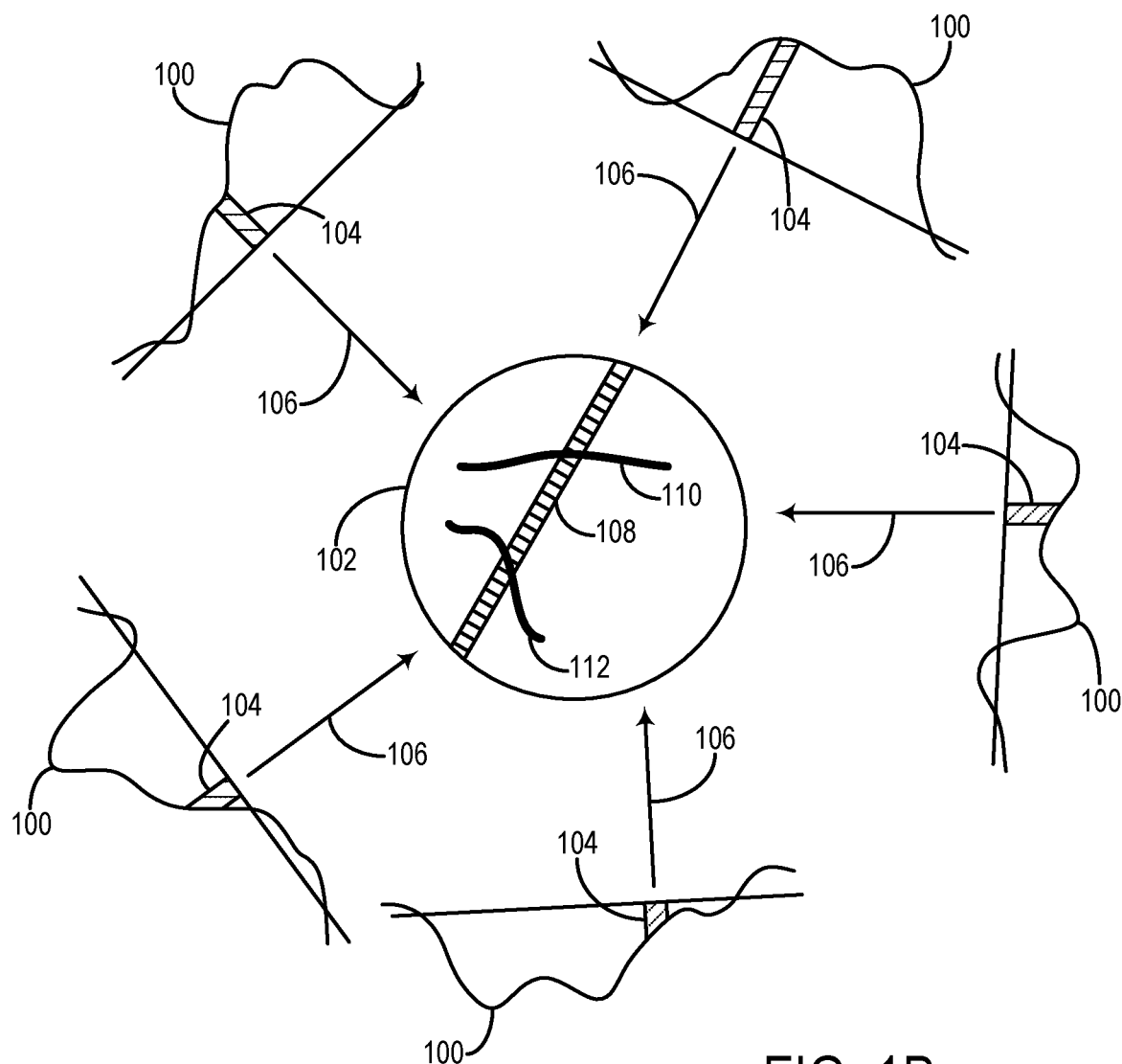
FIG. 1B is a pictorial representation of a conventional backprojection image reconstruction method utilizing HYPR.

HYPR is built upon the discovery that clinically-usable CT image can be produced with far fewer attenuation profiles than demanded by the Nyquist sampling theorem if a priori knowledge of the x-ray attenuation contour in the FOV 102 of FIG. 1A is used in the backprojection process instead of the assumed homogeneous attenuation contour. Referring to FIG. 1B, for example, the attenuation contour in the FOV 102 may be known to include structures such as blood vessels 110 and 112. That being the case, when the backprojection ray path 108 passes through these structures a more accurate distribution of the ray sum 104 in each ray path pixel is achieved by weighting the distribution as a function of the known attenuation contour at that pixel location. As a result, a majority of the ray sum 104 will be distributed in the example of FIG. 1B at the ray path pixels that intersect the structures 110 and 112. For a backprojection ray path 108 having N pixels this may be expressed as follows:

$$\mu_n = (P \times C_n) \bigg/ \sum_{n=1}^{N} C_n; \qquad (2)$$

where: P=the ray sum attenuation value and $C_n$=attenuation value of an a priori composite image at the $n^{th}$ pixel along the backprojection ray path. The numerator in equation (2) weights each pixel using the corresponding attenuation value in the composite image and the denominator normalizes the value so that all backprojected ray sums are given equal weight by the process.

It should be noted that while the normalization can be performed on each pixel separately after the backprojection, in many clinical applications it is far easier to normalize the ray sum attenuation value P before the backprojection. In this case, the ray sum P is normalized by dividing by the corresponding value $P_C$ in a projection through the composite image at the same view angle. The normalized ray sum $P/P_C$ for each view angle is backprojected and summed to form an unconstrained image, and the resulting unconstrained image is then multiplied by the composite image.

Figure 1C:
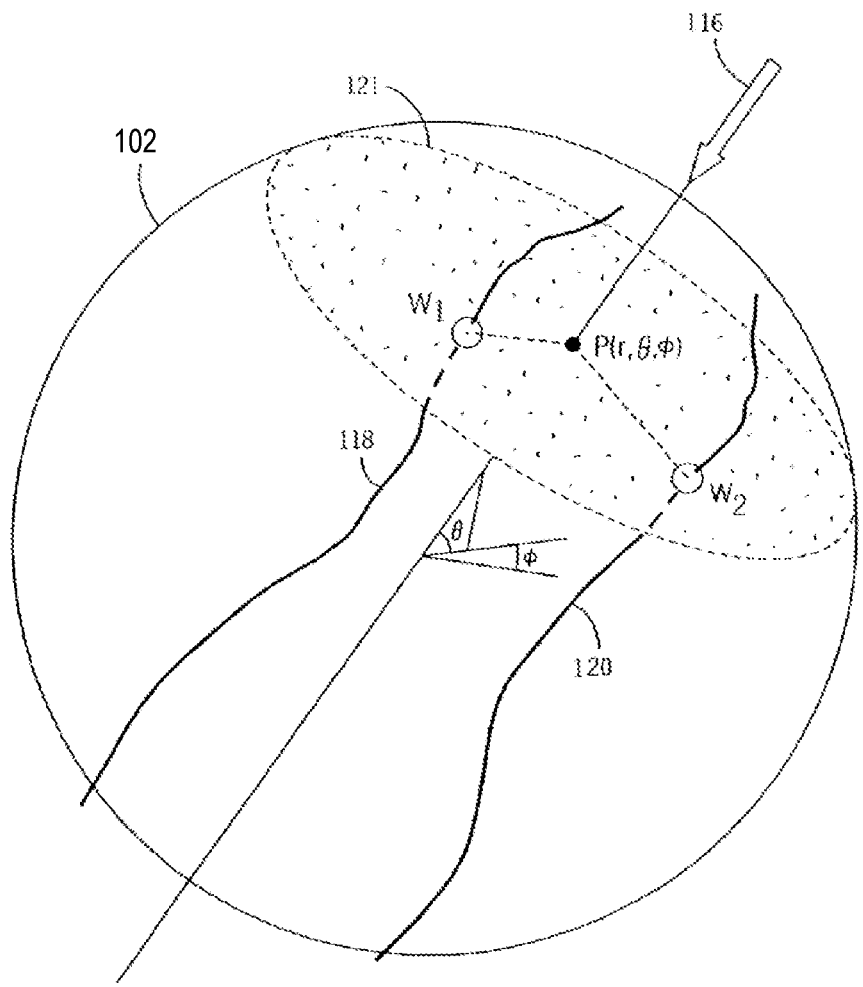
FIG. 1C is a pictorial representation of a 3D backprojection image reconstruction method using HYPR.

A 3D embodiment of the highly constrained backprojection is shown pictorially in FIG. 1C for a single 3D projection view characterized by the view angles θ and φ. This projection view is back projected along axis 116 and spread into a Radon plane 121 at a distance r along the back projection axis 116. Instead of a filtered back projection in which projection signal values are filtered and uniformly distributed into the successive Radon planes, along axis 116, the projection signal values are distributed in the Radon plane 121 using the information in the composite image. The composite image in the example of FIG. 1C contains vessels 118 and 120. The weighted attenuation value is deposited at image location x, y, z in the Radon plane 121 based on the value at the corresponding location x, y, z in the composite image. This is a simple multiplication of the backprojected ray sum value P by the corresponding composite image pixel value. This product is then normalized by dividing the product by the ray sum attenuation value from the corresponding image space projection view of the composite image. The formula for the 3D reconstruction is:

$$I(x,y,z) = \Sigma(P(r,\theta,\phi) * C(x,y,z)_{(r,\theta,\phi)}/P_C(r,\theta,\phi)) \qquad (2a)$$

where the sum (Σ) is over all projections in the image frame being reconstructed and the x, y, z values in a particular Radon plane are calculated using the projection ray sum value $P(r, \theta, \phi)$ at the appropriate r, θ, φ value for that plane. $P_C(r, \theta, \phi)$ is the corresponding ray sum attenuation value from the composite image, and $C(x, y, z)_{(r, \theta, \phi)}$ is the composite image value at (r, θ, φ).

Figure 2:
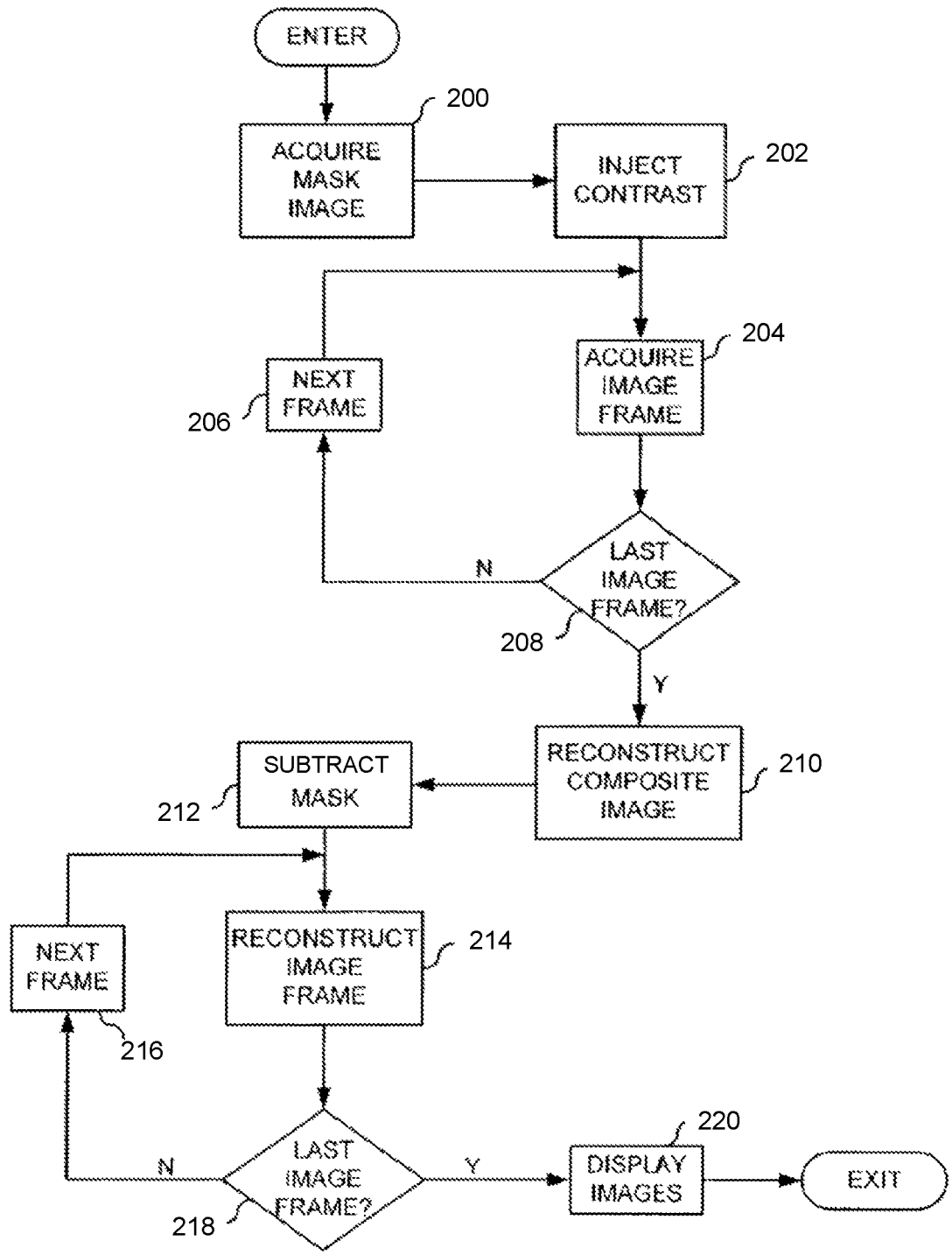
FIG. 2 is a flow chart setting forth some non-limiting example steps of a HYPR process.

Using HYPR, a series of time resolved image frames are acquired when a selected physiological event is occurring in the subject. Referring to FIG. 2, such a process for performing a CT study utilizing HYPR beings, as indicated at process block 200 a mask image is acquired prior to contrast injection. After the mask image is acquired, the contrast agent is injected as indicated at process block 202. A loop is then entered in which a series of frame images are acquired as the contrast agent flows into the region of interest. One cardiac gated image frame is acquired as indicted at process block 204 at the same cardiac phase as the mask image. With the multi-source system, for example, the complete image frame may be acquired in a single 8 msec acquisition and then the sources are rotated to another, interleaved position as indicated at process block 206. When the last image frame has been acquired as indicated at decision block 208, the acquisition phase of the procedure is completed and image reconstruction begins.

Prior to reconstructing the temporally resolved image frames a high resolution composite image is reconstructed as indicated at process block 210. This may be achieved using a conventional filtered backprojection reconstruction of the interleaved projections in all or some of the acquired image frames. Since the image frames are acquired at interleaved view angles, collectively they provide a complete sampling and an artifact-free composite image can be produced using a conventional image reconstruction method. Since the composite image is to be used to reconstruct each image frame, the composite image can be "edited" by subtracting the pre-contrast mask image from it to remove stationary tissues as indicated at process block 212. In addition, to provide a sparse data set for the highly constrained image reconstruction procedure to follow, the individual projection views in each acquired image frame may have the corresponding projection view from the mask image subtracted from it.

The series of time resolved image frames are then reconstructed. A loop is entered in which the limited set of views that comprise an image frame are backprojected using the HYPR method as indicated at process block 214. As will be described, each image frame can be processed as indicated at 216 until the last image frame is reconstructed as determined at decision block 218. The reconstructed image frames may then be displayed as indicated at process block 220. The user may play the entire image frame sequence to observe the inflow of contrast agent into the vasculature of interest or the user may select one or more of the image frames that exhibit the best diagnostic information.

Successive image frames may also be combined to improve image SNR and when 3D image frames are produced, 2D MIP projection images are usually produced from them. As described above the composite image is formed using sets of projections acquired during the dynamic phase of the scan. All or a portion of the sets of acquired projections may be used in forming the composite image, and when the dynamic phase of the scan extends over a longer period of time, this may include one or more sets of projections acquired at the same projection angles. In such case the corresponding values in repeated projection views are averaged to improve SNR.

On the other hand, there are also clinical applications where less than all the acquired sets of interleaved projections are used to reconstruct the composite image. For example, when a contrast agent is employed the subject looks considerably different at different times during the dynamic study. To reflect this change in the subject, more than one composite image may be reconstructed using less than all of the sets of acquired projections so that the composite image is kept up-to-date with the changing subject.

If the frame images are reconstructed after the dynamic scan is completed, the window of acquired image frames used to update the composite image may extend to include image frames acquired after the current image frame. For example, the image frame being reconstructed may be centered in the window with a substantially equal number of other image frames acquired before and after the current image frame. Or, the current image frame may be acquired at the beginning of the window. In this post-processing of the acquired image frames a number of different image frames can be reconstructed in which both the window size and the positioning of the window relative to the current image frame may be varied to achieve the best results.

There are also clinical applications where the composite image may be reconstructed from projections that are acquired prior to the dynamic acquisition phase of the scan. In this case, a high resolution and high SNR composite image is acquired at the beginning of the procedure and reconstructed using a conventional filtered backprojection method. A loop is then entered in which image frames are acquired and displayed. An image frame is acquired with a minimal number of projection views as described above. These projections are aligned, or registered with the composite image to measure translational and rotational motion of the subject. This motion information is used to move the composite image such that it is aligned with the current position of the subject and then the image frame is reconstructed using the registered composite image in the highly constrained backprojection method.

Figure 3:
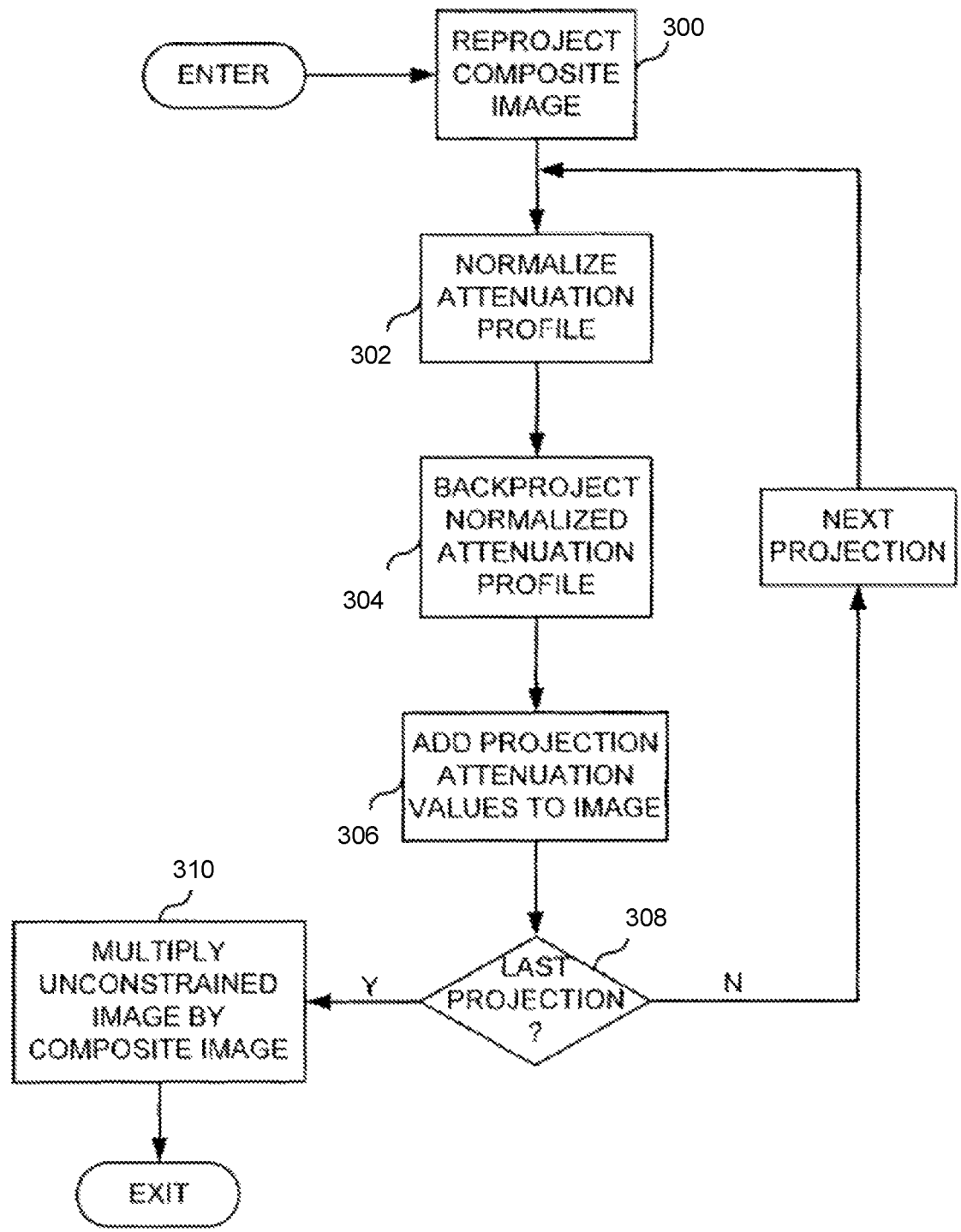
FIG. 3 is a flow chart setting forth some further non-limiting example steps of a HYPR process.

Regardless of the particular acquisition strategies, referring to FIG. 3, a process for HYPR-based CT reconstruction is illustrated. While there are a number of different ways to reconstruct an image frame using HYPR, the process may begin at process block 300 with the re-projection of the composite image. For every attenuation profile P in the current image frame a corresponding composite image attenuation profile $P_C$ is calculated at the same view angle. This re-projection of the composite image is a Radon transformation.

A loop is then entered in which each image frame attenuation profile is normalized at process block 302, backprojected at process block 304, and summed with an unconstrained image frame at process block 306. More specifically, an image frame attenuation profile may be normalized by dividing each attenuation ray sum P by the corresponding attenuation ray sum $P_C$ in the composite image reprojection at the same view angle. This normalized attenuation profile may then be backprojected without any filtering. The resulting unconstrained image values are summed with those back projected from the other attenuation profiles for the current image frame.

When the last attenuation profile has been processed for the current image frame as determined at decision block 308, the reconstructed unconstrained image frame is constrained using the composite image as indicated at process block 310. This is a matrix multiplication in which pixels in the unconstrained image frame are multiplied by the value of corresponding pixels in the composite image. In contrast to prior image reconstruction methods, far fewer projections are needed when the reconstruction method of the present invention is used, and thus, an image frame can be produced very quickly. Image artifacts due to undersampling are suppressed and the higher SNR of the composite image is conveyed to the reconstructed image frame.

Figure 4:
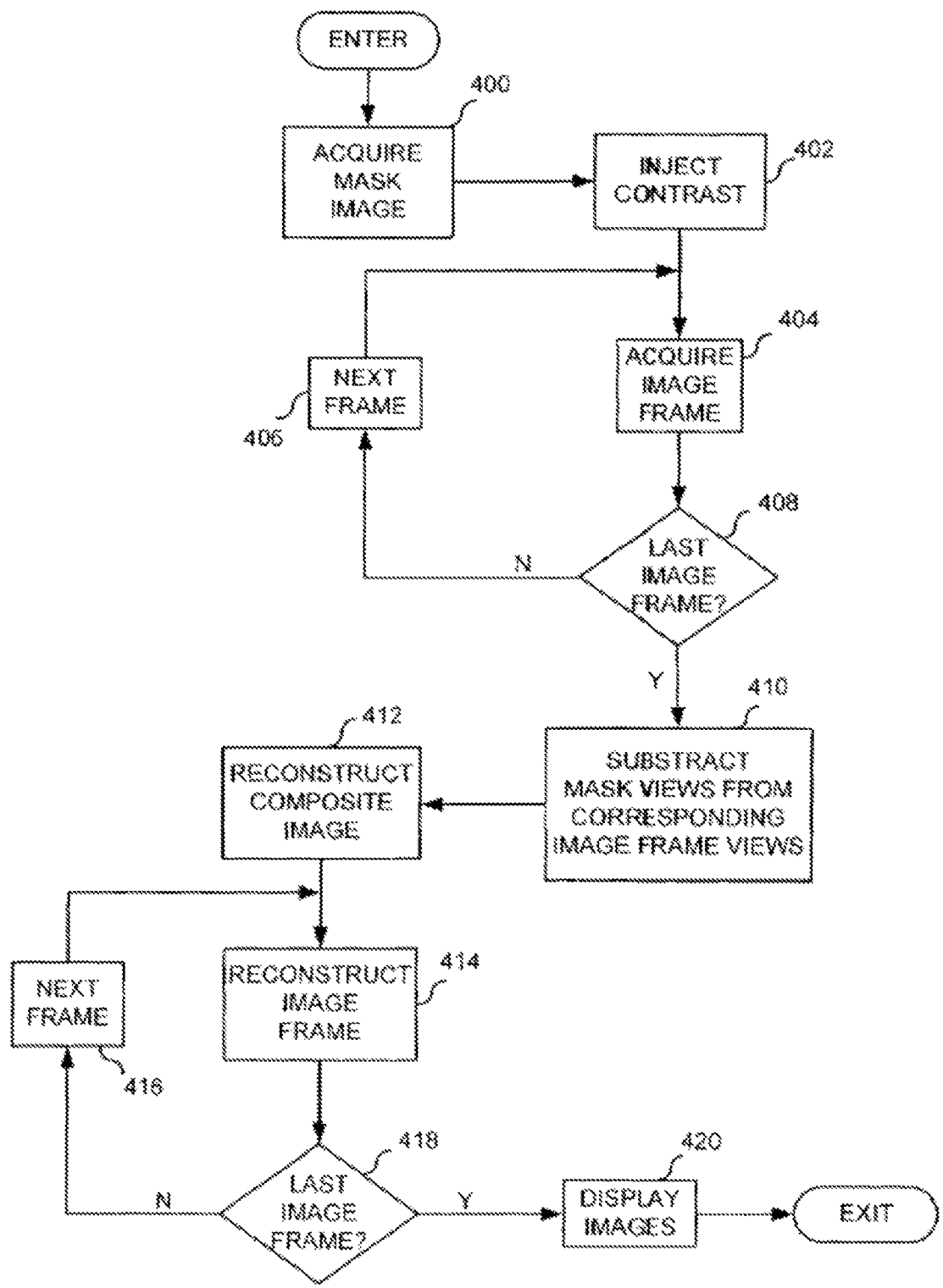
FIG. 4 is a flow chart setting forth some non-limiting example steps of a HYPR process employed to perform a CT angiographic study.

The above-described processes may be adapted for other angiographic procedures, including perfusion studies and the like. In particular, referring to FIG. 4, initial rotations are performed to acquire a pre-injection mask as indicated at process block 400. This mask image may be acquired at full x-ray dose. After the pre-injection mask data is obtained, a contrast agent is administered as indicated at process block 402. The contrast agent can be injected through typical arterial injection, but may also include intravenously introduction.

As indicated at process block 404, a series of image frames are then acquired at a low dose. This may be achieved by rotating the gantry and acquiring a reduced number of projection views during the revolution. For example, whereas 400 projection views might be acquired during a normal scan, a substantially reduced number of projection reviews, such as only 40 projection views, may be acquired during this low-dose acquisition. As determined at decision block 408, this is repeated as indicated at process block 406 until all of the desired image frames are acquired.

In this non-limiting example, of each image frame being comprised of 40 views, the x-ray dose which the subject receives is only one-tenth the x-ray dose that would be received if a fully sampled image (e.g., 400 views) were acquired for each image frame. Alternatively, each image frame may be acquired as a full set of 400 projection views. However, in this approach a lower x-ray dose is delivered to the subject by reducing the intensity of the x-ray beam produced by the x-ray source. This is achieved by, for example, reducing the x-ray tube current. Of course, by reducing the x-ray beam strength in this manner one would expect the SNR of the resulting reconstructed image to be reduced by a corresponding amount. By performing a highly constrained backprojection as described below, however, the lost SNR is recaptured.

After the image frames are acquired using either of the above-described low dose methods, the acquired mask projection views are subtracted as indicated at process block 410. This is a subtraction from attenuation values in each acquired image frame projection view of corresponding attenuation values in the mask image projection acquired at the same view angle. The resulting image frame projection views indicate the difference in x-ray attenuation caused by perfusion of the contrast agent into the tissues being examined.

Prior to reconstructing the perfusion images a high resolution composite image is reconstructed as indicated at process block 412. This is a filtered backprojection reconstruction using the difference projection views from all of the acquired image frames. Since the image frames are acquired at interleaved view angles in the first embodiment, collectively they provide a complete sampling of Radon space and an artifact-free, high SNR composite image can be produced with a standard reconstruction method. In the second approach described above the corresponding low-dose views acquired for each image frame are averaged to provide a higher SNR composite image than would otherwise be produced from one complete set of low dose views.

The series of time resolved perfusion image frames are then reconstructed and displayed. A loop is entered in which the limited set of difference views that comprise an image frame are backprojected using the highly constrained method as indicated at process block 414. Each perfusion image frame is reconstructed as indicated at 416 until the last perfusion image frame is reconstructed as determined at decision block 418. The reconstructed perfusion image frames may then be displayed as indicated at process block 420 or further processed to provide images indicative of tissue health.

Figure 5A:
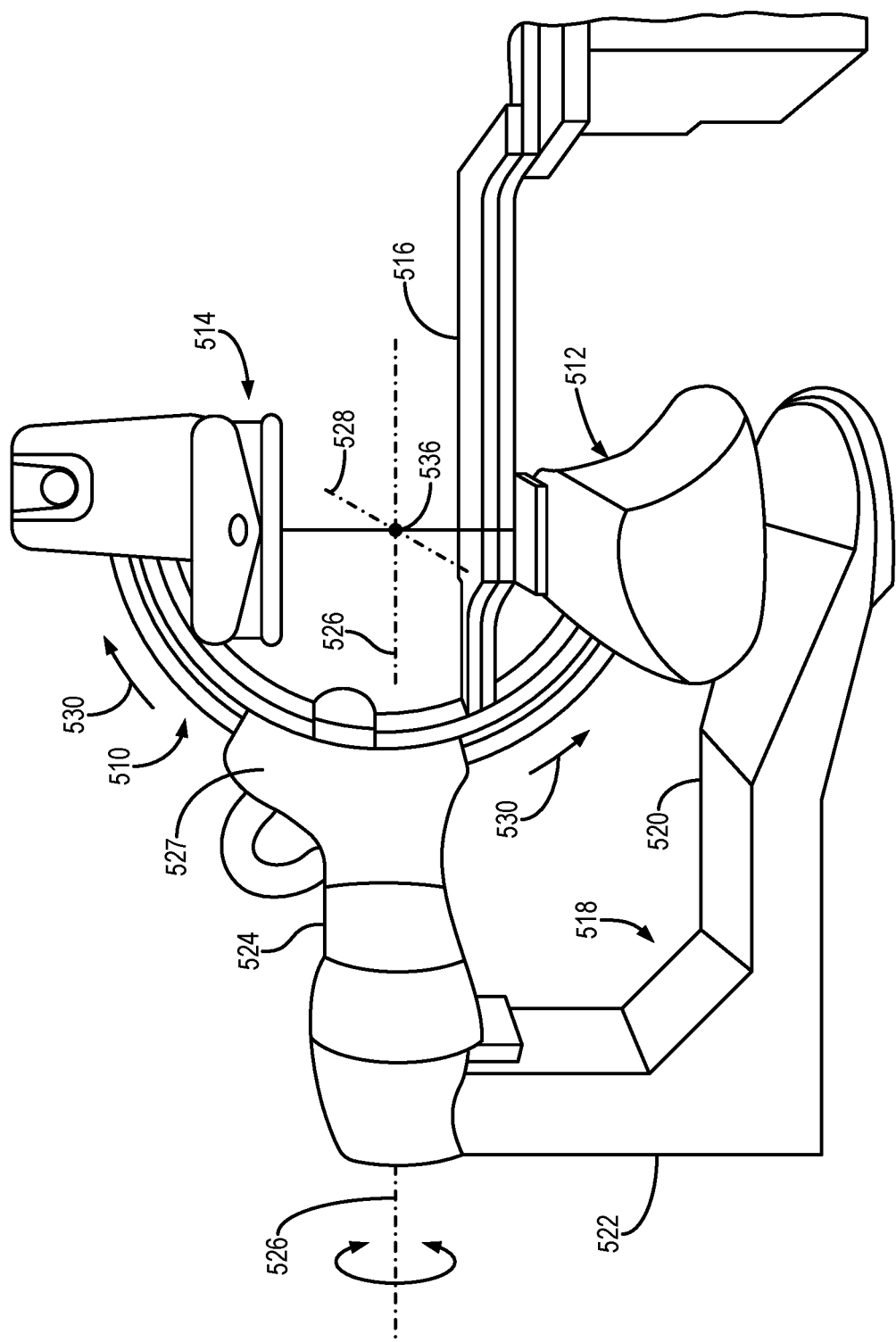
FIG. 5A is a perspective view of a rotational, C-arm x-ray system configured to carry out a 4D DSA process.

CT images may be acquired by any of a variety of systems. Referring to FIG. 5A, a rotational x-ray system is illustrated that is specifically designed for use in connection with interventional procedures. It is characterized by a gantry having a C-arm 510 which carries an x-ray source assembly 512 on one of its ends and an x-ray detector array assembly 514 at its other end. The gantry enables the x-ray source 512 and detector 514 to be oriented in different positions and angles around a patient disposed on a table 516, while enabling a physician access to the patient.

The gantry includes an L-shaped pedestal 518 which has a horizontal leg 520 that extends beneath the table 516 and a vertical leg 522 that extends upward at the end of the horizontal leg 520 that is spaced from of the table 516. A support arm 524 is rotatably fastened to the upper end of vertical leg 522 for rotation about a horizontal pivot axis 526. The pivot axis 526 is aligned with the centerline of the table 516 and the arm 524 extends radially outward from the pivot axis 526 to support a C-arm drive assembly 527 on its outer end. The C-arm 510 is slidably fastened to the drive assembly 527 and is coupled to a drive motor (not shown) which slides the C-arm 510 to revolve it about a C-axis 528 as indicated by arrows 530. The pivot axis 526 and C-axis 528 intersect each other at an isocenter 536 located above the table 516 and they are perpendicular to each other.

The x-ray source assembly 512 is mounted to one end of the C-arm 510 and the detector array assembly 514 is mounted to its other end. The x-ray source 512 emits a beam of x-rays which are directed at the detector array 514. Both assemblies 512 and 514 extend radially inward to the pivot axis 526 such that the center ray of this beam passes through the system isocenter 536. The center ray of the beam can thus be rotated about the system isocenter around either the pivot axis 526 or the C-axis 528, or both during the acquisition of x-ray attenuation data from a subject placed on the table 516.

The x-ray source assembly 512 contains an x-ray source which emits a beam of x-rays when energized. The center ray passes through the system isocenter 536 and impinges on a two-dimensional flat panel digital detector housed in the detector assembly 514. The detector 538 may, for example, be a 2048 by 2048 element two-dimensional array of detector elements having a size of 41 cm by 41 cm. Each element produces an electrical signal that represents the intensity of an impinging x-ray and hence the attenuation of the x-ray as it passes through the patient. During a scan the x-ray source assembly 512 and detector array assembly 514 are rotated about the system isocenter 536 to acquire x-ray attenuation projection data from different angles. The detector array is able to acquire 530 projections, or views, per second and this can be the limiting factor that determines how many views can be acquired for a prescribed scan path and speed.

Figure 5B:
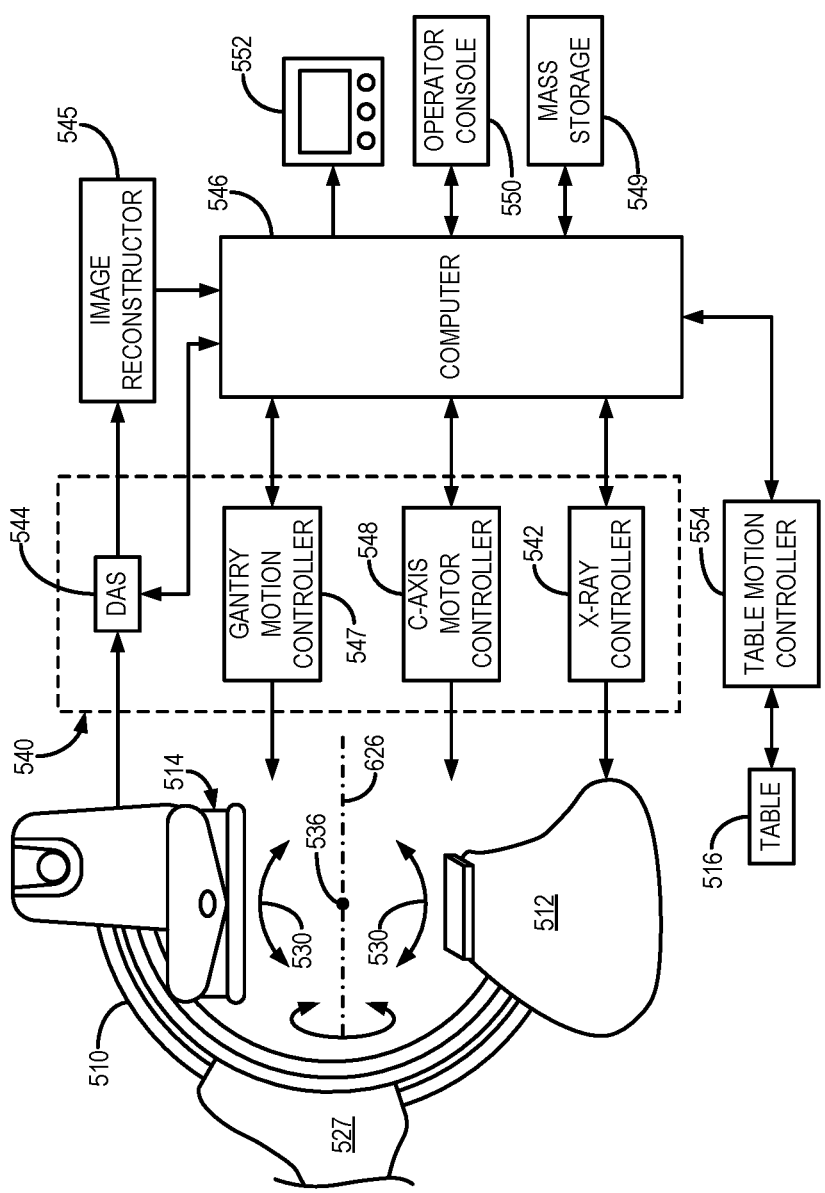
FIG. 5B is a schematic view of the C-arm x-ray system of FIG. 5A.
Figure 6A:
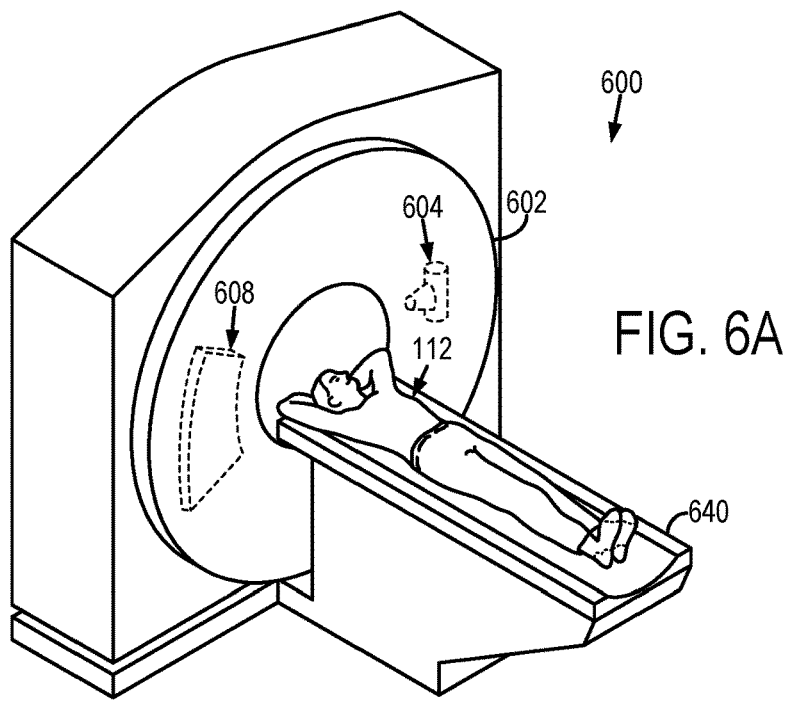
FIG. 6A is a perspective view of a gantry-based CT system that, in accordance with the present disclosure, can be utilized to perform ultrafast quantitative CT angiography.
Figure 6B:
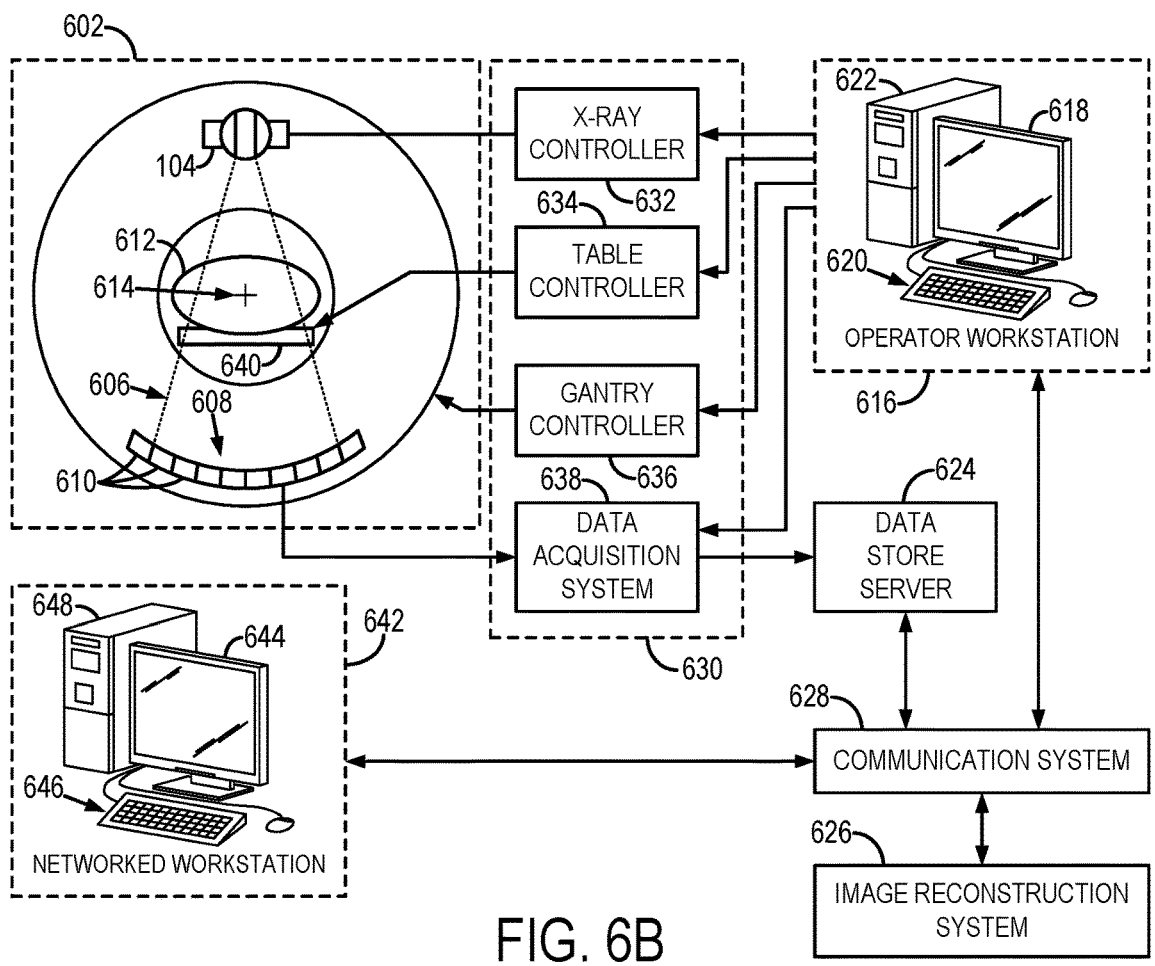
FIG. 6B is a schematic view of the CT system of FIG. 6A.

Referring particularly to FIG. 5B, the rotation of the assemblies 512 and 514 and the operation of the x-ray source are governed by a control system 540 of the x-ray system. The control system 540 includes an x-ray controller 542 that provides power and timing signals to the x-ray source 532. A data acquisition system (DAS) 544 in the control system 540 samples data from detector elements 538 and passes the data to an image reconstructor 545. The image reconstructor 545, receives digitized x-ray data from the DAS 544 and performs high speed image reconstruction according to the methods of the present invention. The reconstructed image is applied as an input to a computer 546 which stores the image in a mass storage device 549 or processes the image further to produce parametric images according to the teachings of the present invention. It is contemplated that the computer 546 may be or include components of a digital vascular image processor (DVIP) system.

The control system 540 also includes gantry motor controller 547 and a C-axis motor controller 548. In response to motion commands from the computer 546 the motor controllers 547 and 548 provide power to motors in the x-ray system that produce the rotations about respective pivot axis 526 and C-axis 528. As will be discussed below, a program executed by the computer 546 generates motion commands to the motor drives 547 and 548 to move the assemblies 512 and 514 in a prescribed scan path.

The computer 546 also receives commands and scanning parameters from an operator via console 550 that has a keyboard and other manually operable controls. An associated cathode ray tube display 552 allows the operator to observe the reconstructed image and other data from the computer 546. The operator supplied commands are used by the computer 546 under the direction of stored programs to provide control signals and information to the DAS 544, the x-ray controller 542 and the motor controllers 547 and 548. In addition, the computer 546 operates a table motor controller 554 which controls the motorized table 516 to position the patient with respect to the system isocenter 536.

Figures 9A, 9B:
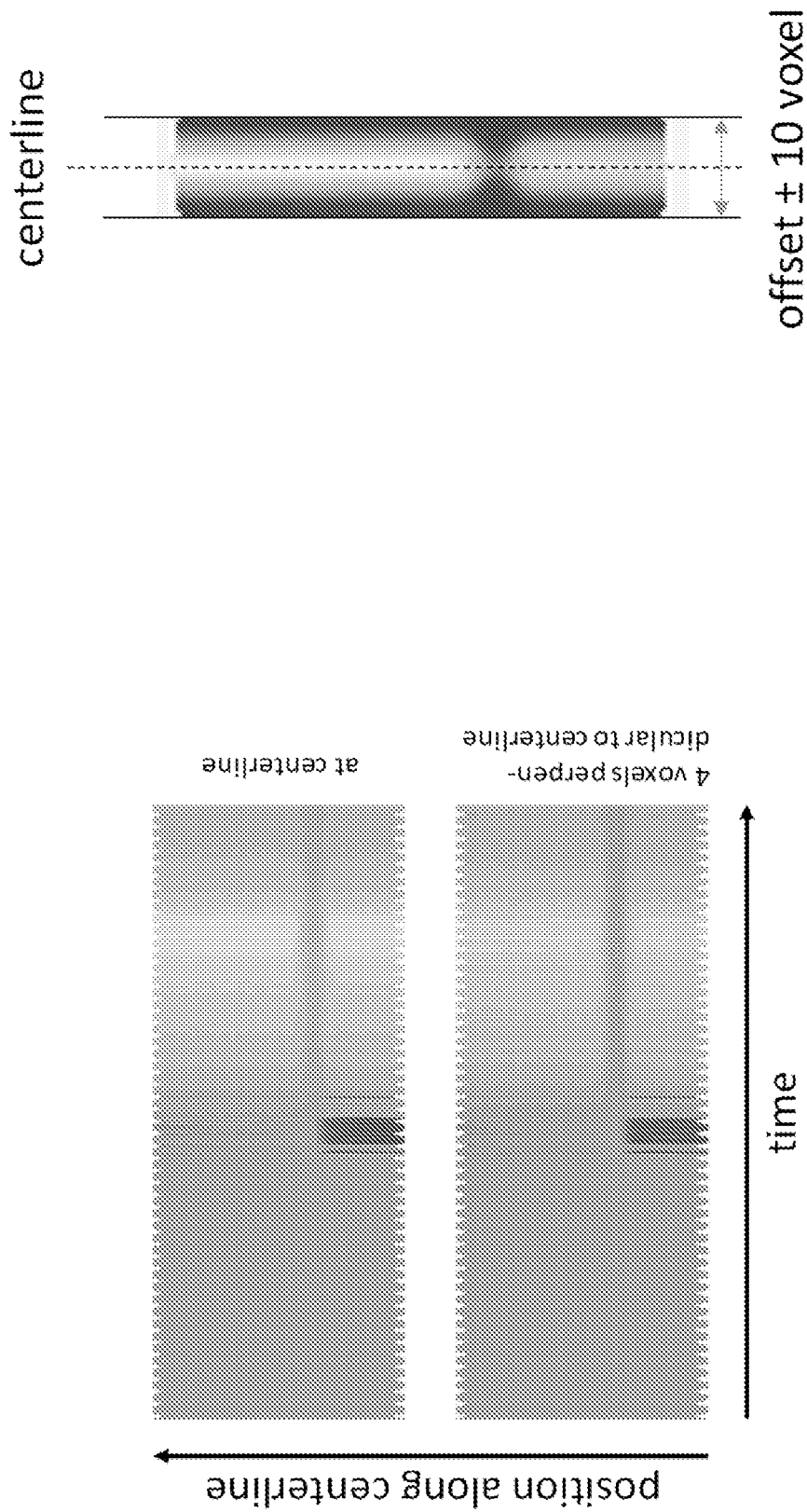
FIG. 9A is an illustration of time-attenuation information in time and position.
FIG. 9B is an illustration of a vessel used to create the illustration of FIG. 9A.

Another example of a CT system is illustrated in FIGS. 9A and 9B, which provide a CT system 600 that, as will be described, includes a rapid-rotation CT gantry 602 that includes at least one x-ray source 604 arranged to direct an x-ray beam 606, which may be a fan-beam or cone-beam of x-rays, toward a large-area detector array 608.

The detector array 608 includes a number of x-ray detector elements 610. As described, the detector array 608 may have a large area and, thus, a corresponding number of detector elements 610. For example, the large-area detector array may 608 achieve a data acquisition of 256-320 slices simultaneously. Together, the x-ray detector elements 610 sense the projected x-rays 606 that pass through a subject 612, such as a medical patient or an object undergoing examination, which is positioned in the CT system 600. Each x-ray detector element 610 produces an electrical signal that may represent the intensity of an impinging x-ray beam and, hence, the attenuation of the beam as it passes through the subject 612. In some configurations, each x-ray detector 610 is capable of counting the number of x-ray photons that impinge upon the detector 610. During a scan to acquire x-ray projection data, the gantry 602 and the components mounted thereon rotate about a center of rotation 614 located within the CT system 600.

The CT system 600 also includes an operator workstation 616, which typically includes a display 618; one or more input devices 620, such as a keyboard and mouse; and a computer processor 622. The computer processor 622 may include a commercially available programmable machine running a commercially available operating system. The operator workstation 616 provides the operator interface that enables scanning control parameters to be entered into the CT system 600. In general, the operator workstation 616 is in communication with a data store server 624 and an image reconstruction system 626. By way of example, the operator workstation 616, data store server 624, and image reconstruction system 626 may be connected via a communication system 628, which may include any suitable network connection, whether wired, wireless, or a combination of both.

As an example, the communication system 628 may include both proprietary or dedicated networks, as well as open networks, such as the internet.

The operator workstation 616 is also in communication with a control system 630 that controls operation of the CT system 600. The control system 630 generally includes an x-ray controller 632, a table controller 634, a gantry controller 636, and a data acquisition system 638. The x-ray controller 632 provides power and timing signals to the x-ray source 604 and the gantry controller 636 controls the rotational speed and position of the gantry 602. The table controller 634 controls a table 640 to position the subject 612 in the gantry 602 of the CT system 600.

The DAS 638 samples data from the detector elements 610 and converts the data to digital signals for subsequent processing. For instance, digitized x-ray data is communicated from the DAS 638 to the data store server 624. The image reconstruction system 626 then retrieves the x-ray data from the data store server 624 and reconstructs an image therefrom. The image reconstruction system 626 may include a commercially available computer processor, or may be a highly parallel computer architecture, such as a system that includes multiple-core processors and massively parallel, high-density computing devices. Optionally, image reconstruction can also be performed on the processor 622 in the operator workstation 616. Reconstructed images can then be communicated back to the data store server 624 for storage or to the operator workstation 616 to be displayed to the operator or clinician.

The CT system 600 may also include one or more networked workstations 642. By way of example, a networked workstation 642 may include a display 644; one or more input devices 646, such as a keyboard and mouse; and a processor 648. The networked workstation 642 may be located within the same facility as the operator workstation 616, or in a different facility, such as a different healthcare institution or clinic. Data may be exchanged between components of the CT system 600 in any suitable format, such as in accordance with the transmission control protocol ("TCP"), the internet protocol ("IP"), or other known or suitable protocols.

The detector array 608 may have a large area and, thus, a corresponding number of detector elements 610. Again, the large-area detector array may 608 achieve a data acquisition of 256-320 slices simultaneously. Thus, utilizing the above-described CT system 600, full CT images can be generated at rates on the order of 3 per second. Each volume is acquired using about 300 projections. So, for a 0.3 second acquisition the projection duration is about 1 millisecond. Using this system 600, constraining volumes can be generated from each of the vascular volumes obtained during the sequential rotations of the gantry 602. Optionally, a constraining image can be generated from all the vascular volumes obtained over a 5-10 second series of rotations (up to about 30 volumes). When the shorter-term constraining images are used, the constraining image is sparser and leads to improved reconstruction from the projections used to form it.

Figure 7:
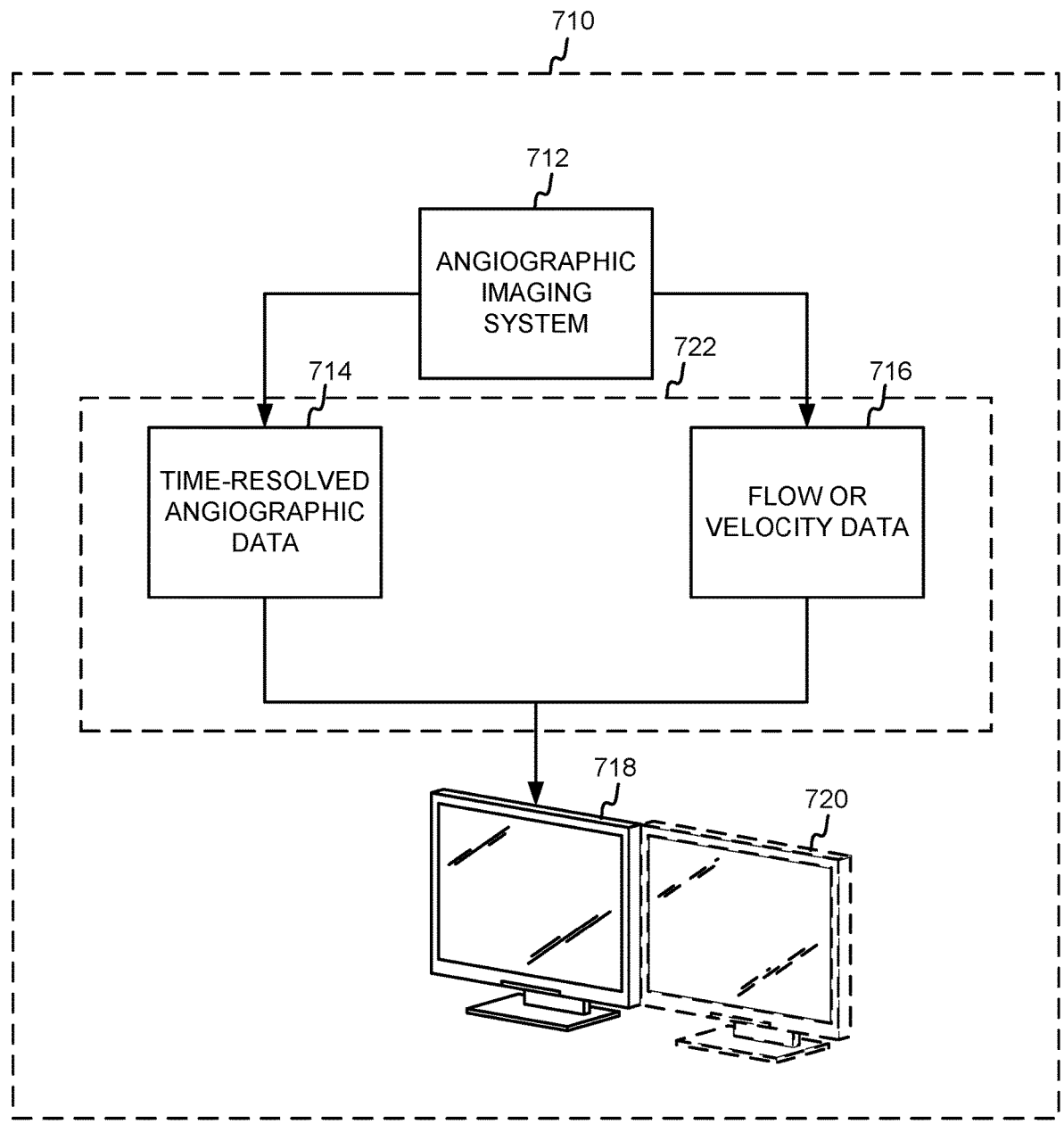
FIG. 7 is a schematic view of an angiographic processing and display system that may include the system of FIGS. 6A and 6B to provide quantitative CT angiography images.

Irrespective of the particular hardware used to acquire the image data, the present disclosure provides systems and methods for calculating or determining flow or velocity information non-invasively, using image-derived information. Referring to FIG. 7, such system 710 is provided. In particular, the system 710 includes an angiographic imaging system 712. The angiographic imaging system 712 is the CT system described above, which can be conceptualized as delivering time-resolved angiographic data 714 and flow or velocity data 716. The time-resolved angiographic data 714 and flow or velocity data 716 can be processed and provided to a clinician via a display 718. As will be further described, the information may be provided to the clinician using multiple displays including a first display 718 and a secondary display 720 or multiple additional displays. As will also be described, the process of deriving velocity or flow data can be performed partially or in whole using an image processing system, which may include a graphics processing unit (GPU) or other processor, including a central processing unit (CPU).

The above-described system 710 can be used to acquire raw angiographic data that can then be processed to determining vascular velocity using angiographic images and techniques. For example, velocity maps can generated using a highly constrained imaging from projections (HYPR) angiography reconstruction. In some configurations, local velocity maps can be generated using local area information or using local time of arrival estimates. Local-HYPR techniques may be used.

The systems and methods provided above for generating velocity maps find use in, for example, generating vascular pressure maps, for improving accuracy of computational fluid dynamics by providing improved velocity boundary conditions, and for generating coronary flow reserve (CFR) values. The derived velocity maps can be used to generate a local velocity map using flow continuity within a vascular branch and the measured cross-sectional area or local time of arrival estimates.

That is, the local velocity map provides flow information of a local region. As will be described, in some non-limiting implementations, the local region can be the size of a pixel (e.g., 0.5 mm). In some configurations, the local region can be from 0.5 mm to 50 mm in size (e.g., 0.5 mm, 1 mm, 1.5 mm, 2 mm, 5 mm, 10 mm, 20 mm, 30 mm, 40 mm, 50 mm; and any values therein between).

In some configurations, information can be provided for a first region and a second region that are neighboring regions. Where the regions are larger (e.g., 50 mm), the local velocity map may be a coarser velocity map. However, such maps find use in certain applications. A coarser map can be achieved, for example, employing a wide area scanner producing about ten CTA's per second. With ten CTA's per second a 0.1 sec time difference corresponding to a spacing of approximately 500 mm/sec*0.1 sec=50 mm can be employed.

This new physiological information, that is added to the usual CTA anatomical information, can be used in combination with Navier-Stokes equations to produce immediate model-independent estimate of fractional flow reserve (FFR) without the need for computational fluid dynamics or deep learning algorithms. As used herein, FFR is a ratio of maximum blood flow distally to a stenosis or vessel condition relative to normal maximum flow in the same vessel. Thus, FFR can be calculated as pressure distally to the vessel condition over pressure proximal to the vessel condition, where the vessel condition may be the stenosis or other vessel state that may cause a change in pressure. The present disclosure recognizes that FFR can be calculated non-invasively using medical imaging data and a model for flow or velocity through the vessel.

Models

Incompressible Navier-Stokes for fluids with uniform density (assuming constant velocity):

$$\nabla p = \rho[\nu \Delta u + f - (u \cdot \nabla)u] \qquad (3);$$

wherein p is the pressure, f is body force (external forces that act on the particles), u is the velocity vector field, and ρ and ν are the density and the kinematic viscosity of blood, respectively Without the diffusive term (assuming influence diffusion is negligible):

$$\nabla p = -\rho(u \cdot \nabla)u \quad (4).$$

The systems and methods were demonstrated in an animal model as described below. Combined with near-zero dose CT fluoroscopy, the technology provided herein provides systems and methods for new interventional platforms, providing model-independent flow reserve and FFR estimates that find use for planning immediate interventions and for observing, analyzing, and modifying interventions.

In some configurations, the velocity maps are generated using a HYPR approach. In some configurations, the velocity maps are generated not using a HYPR approach. For example, in the latter case, in some configurations, a series of time images are obtained using a CT scanner with FBP reconstruction. Centerlines and signal curves are determined using segmentation of blood vessels in FBP images (instead of LV background subtraction). Interpolation can be used to create intermediate points on time curves. The average branch velocity and flow is determined. Flow continuity can be used to generate a local velocity map.

In some configurations, provided herein are systems and methods for generating arterial flow signals based on computed tomography projections that include obtaining an image of an anatomical region including a coronary artery structure.

As described, current systems and methods for generating CT-based FFR data has been has shortcomings that make it limited in clinical utility. Nevertheless, FFR, if available and reliable, can be an important tool to address the broadest range of patients, including those with microvascular disease. The systems and methods provided herein provide CFR and FFR determinations with significantly fewer model-independent assumptions. The systems and methods herein also find use to provide improved boundary condition information to improve the speed and accuracy of presently available CFD methods for CT-FFR.

As described above, HYPR exploits the sparsity of the angiographic data set and reconstructed time frames by back-projecting an undersampled projection data set into a constraining image formed from all acquired data. Conventional imaging and reconstruction methods use just the projections acquired during the time frame to perform a filtered back projection. HYPR-based reconstruction takes these projections and does an unfiltered back projection, depositing the projection information only in those voxels contained in the constraining image. These images were acquired with a "stack of stars" technique in which radial acquisition is performed in a series of slices. Thus, clinically suitable images can be acquired with a factor of 50 reduction in the Nyquist sampling requirement.

Figure 8A:
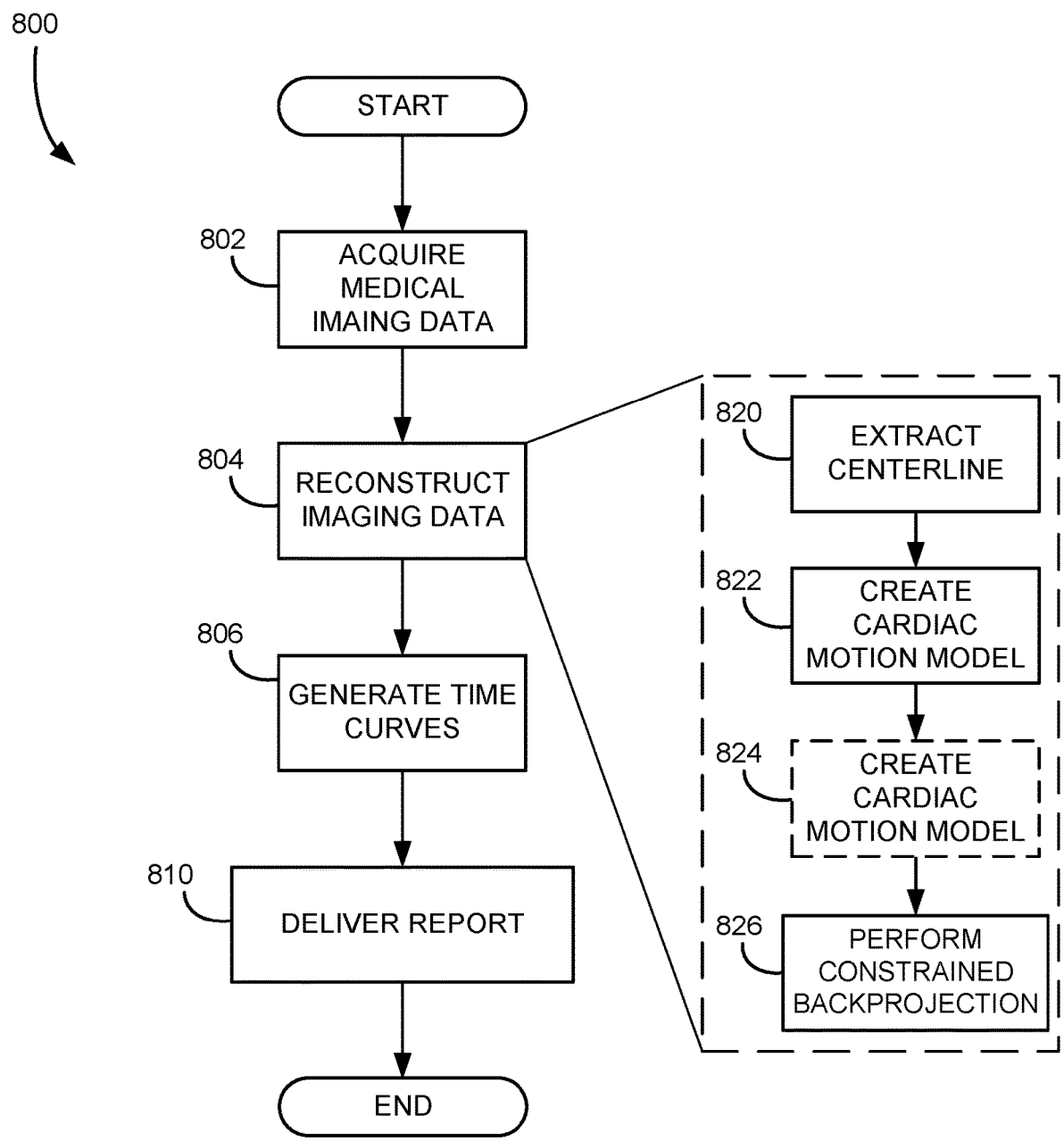
FIG. 8A is a flow chart setting forth some non-limiting example steps of a process in accordance with the present disclosure.

Referring now to FIG. 8, a flow chart is provided that sets out some non-limiting, example steps 800 of a process in accordance with the present disclosure. At process block 802, medical imaging data is acquired. More particularly, the medical imaging data may include helical CTA data and perfusion data. In one non-limiting example, a CT data acquisition may be performed to acquire, on the order of 1000 projections per rotation with 2-3 rotations per second. For the calculation of coronary velocities, cine acquisitions may be performed in which multiple rotations are performed during the first pass of IV contrast. Typically, ten seconds of contrast uptake may be analyzed.

At process block 804, a HYPR-based reconstruction may be performed. By suing HYPR-based reconstruction, the data acquired at process block 802 can produce on the order of 2500 CTA volumes per second. The HYPR-based reconstruction methods facilitate the use of undersampling in the case of HYPR CTA, which relates to the generation of vascular volumes using single projections in combination with a constraining volume containing just the vascular structures. The constraining volume may be formed from all acquired projections, or less than all acquired projections. Then, an LV background subtraction is performed and individual projections are convolved with a 2D spatial kernel, typically a square kernel of 10-20 pixels. This convolution is done so that the signal to noise ratio (SNR) of the HYPR CTA time frame is dominated by the SNR of the constraining image and not by the SNR of the individual projections. For conventional CT acquisition, these are typically ~1000 projections per rotation and 2-4 rotations per second so there are 2000 or more time frames per second. These projections are backprojected without filtration into the constraining image to generate the HYPR CTA vascular volumes.

In some configurations, where a HYPR-based reconstruction is employed, HYPR CCTA reconstruction is carried out. In some configurations, this involves segmentation of coronaries in helical CTA. This process can be carried out manually or may be automated using, for example, deep learning-based automated techniques. In some configurations, the process may include, at process block 820, extracting a centerline from segmentation using topology preserving thinning or other surface based approaches. The process continues at process block 822 by creating a cardiac motion model of coronaries. In one implementation, creating the model may include reconstructing retrospectively gated 3D images from cine acquisitions at different cardiac phases (e.g., 10 phases) and tracking coronaries (e.g., semi-automatically by manually defining several points for each coronary branch in the 3D reconstructions followed by an affine registration approach).

Then, at optional process block 824, a respiratory motion model (if desired or necessary) may be created. As a non-limiting example, the respiratory model may be created by reconstructing retrospectively gated 3D images from cine acquisitions at the same cardiac phase (e.g., 70% R-R) at different time points and then tracking coronaries (e.g., semi-automatically by manually defining several points for each coronary branch in the 3D reconstructions followed by an affine registration approach).

At process block 826, a constrained back projection may be performed for each projection image. This may be achieved by extracting a cardiac state from ECG signal and performing an optional "mask subtraction." That is, optionally, a masks subtraction may be performed by finding a corresponding early image (without iodine signal) at the same angle and similar cardiac state and subtracting images. Whether or not a mask subtraction is performed, process block 826 may be further implemented by applying cardiac (and respiratory) motion models to vessel centerlines and projecting centerlines into a 2D projection and interpolating values along the centerlines. Then, optionally, an "overlap subtraction" may be performed by interpolating values at distance, d, orthogonal from the centerline, and subtracting from the centerline value to remove the influence of overlapping structures such as the left ventricle. Furthermore, the process may include an optional processing step for dual source scanners, to perform interpolation for both simultaneously acquired images and creating a final value from the minimum or, alternatively, mean, max or other functions may be used). In some configurations, the interpolated values for each point along the centerlines (with or without additional overlap subtraction or dual source) reflect the 4D signal values for time, t, where the projection image was acquired.

Then, returning to the overall process flow at process block 806, the reconstructed data is used to generate time curves for velocity and flow analysis. For example, coronary artery velocities can be determined. The data employed for generation of the signal curves used to derive coronary artery velocities can be acquired using a CTA helical scan, followed by a perfusion scan obtained during a first pass of IV contrast. The technology is not limited to a particular contrast agent or dose used. Any suitable CT contrast agent and dose that provides resolvable data may be employed. However, it should be noted that an advantage of the systems and methods provided herein is the ability to use lower doses of contrast relative to other techniques.

The calculation of coronary velocities involves the use of cine acquisition in which multiple rotations are performed during the first pass of IV contrast. Typically, ten seconds of contrast uptake are analyzed. In some configurations, calculation of CFR involves two such runs, one at rest and one at stress. A typical X-ray dose for a ten second cine scan is approximately 0.55 mSv. Using standard perfusion acquisition, calculations of CFR involves twice that amount.

In some configurations, the generation of time-attenuation curves can be carried out following data acquisition. In some configurations, the data acquisition used for generation of time-attenuation curves can include the steps of bolus timing, CCTA data acquisition, and cine acquisition (e.g., under rest and stress states). In some configurations, bolus timing is conducted to determine a delay between the start of an injection and arrival of contrast (e.g., iodine) in the coronary arteries. In some configurations, helical coronary CT angiogram (CCTA) is carried out using acquisition and iodine injection protocols. In some configurations, cine acquisitions during contrast injection can be determined to capture dynamic increase of contrast in the coronaries at: a) rest condition (without additional vasodilation, e.g., administration of adenosine, nitro glycerine, etc.); and b) stress condition if CFR calculations are desired (with vasodilation).

Finally, at process block 810, a report may be delivered using the images and/or time curves described above to communicate flow and/or velocity information. The report may be communicated, for example, via display using the above-described systems, which include display systems.

Figure 8B:
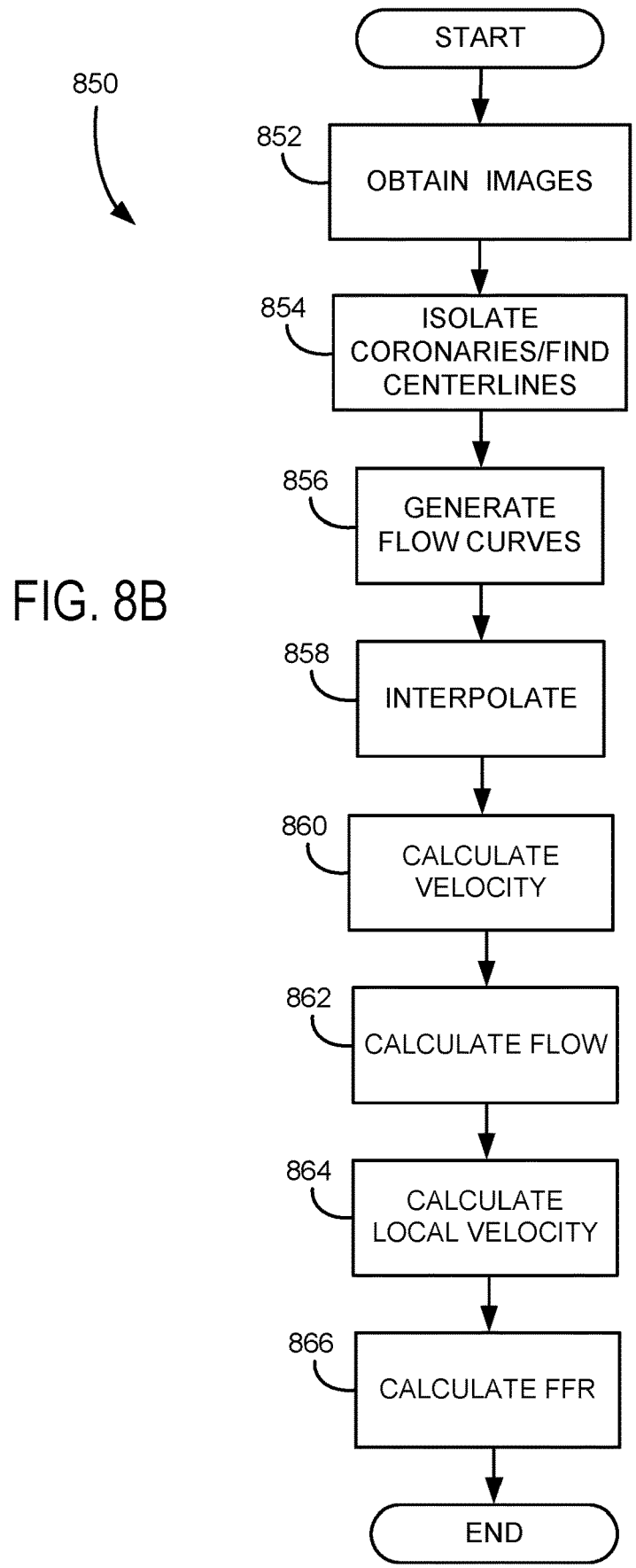
FIG. 8B is a flow chart setting forth some non-limiting example steps of a process for calculating FFR in accordance with the present disclosure.

Referring now to FIG. 8B, one specific example 850 of implementing the above-described process for the purpose of calculating FFR is illustrated. Specifically, the process starts at process block 852 with the acquisition of images. These maybe acquired and reconstructed using a HYPR-based reconstruction or a filtered backprojection (FBP) reconstruction. In the latter case, it may be advantageous to acquire, for example, 6 FPB reconstructed images per second. Then, at process block 854, the coronaries are isolated in the images and the centerlines of each branch desired for velocity or flow calculations are identified. At process block 856, flow curves are generated for each, for example, with 6 points per second. At process block 858, interpolation is performed, for example, interpolating to 24 points per second giving 40 mseconds of separation, which at 500 mm/sec gives roughly 2 cm for the shortest branches. At process block 860, velocity, such as average velocity, is calculated and, flow direction is determined at process block 862. Based thereon, at process block 864, local velocity can be determined. Using these calculations, FFR can then be determined.

EXAMPLES

In one non-limiting example, an axial CT scan was performed on a subject. The rotation time was 0.4 seconds using a contrast injection of 10 ml at 2.1 ms/s and a saline injection of 8 ml at 1.0 ml/s. HYPR-based CTA reconstruction was used to create images from the acquired data. Using the images, time-attenuation curves were created for each point along the centerline of a given vessel (see FIG. 9A), as well as for points along perpendicular to the vessel profile (see FIG. 9B).

Figure 9D:
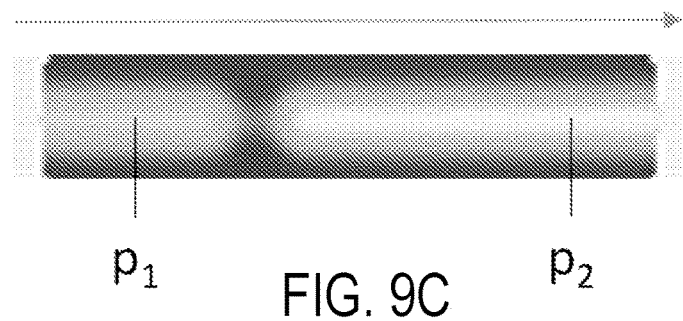
FIG. 9D is a graph comparing stenosis in phantom models.
Figure 9D:
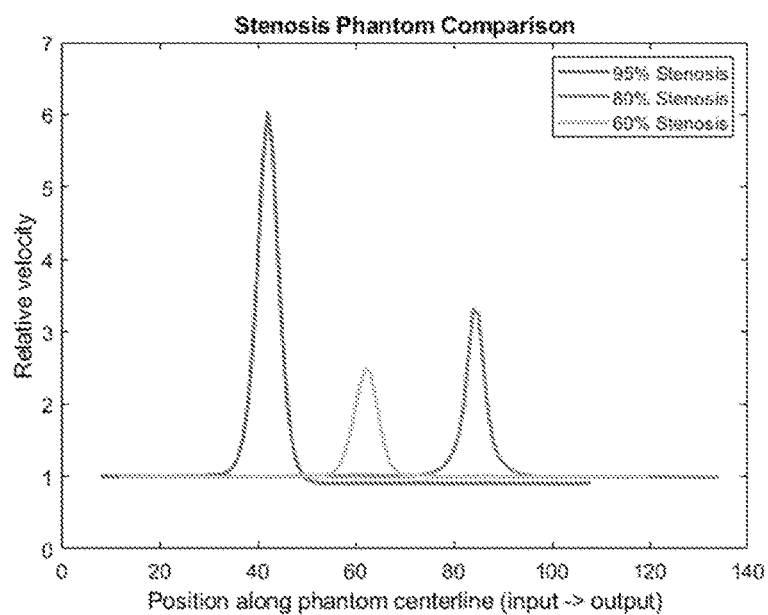

Then, flow conservation was used to calculate the relative average cross-section velocities assuming that the same amount of contrast passes through every cross-sectional plane. As illustrated in FIG. 9C, the total amount of contrast medium (the sum over time) is the same for $p_1$ and $p_2$. With this, as illustrated in FIG. 9D, the some over time and across the vessel profile at each point gives the total attenuation, which is proportional to the average amount of time one particle needs to travel through the cross-sectional area (inverse velocity).

Figure 9E:
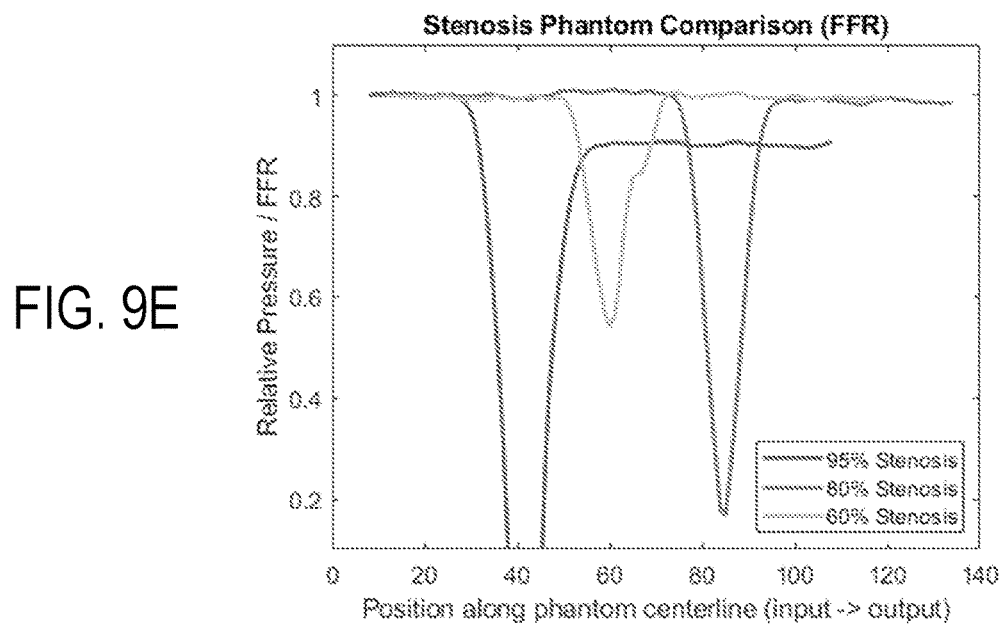
FIG. 9E is a graph comparing FFR calculations for the phantom models of FIG. 9D.

Using this information, as illustrated in FIG. 9E, the pressure drop can be determined. For example, the Navier-Stokes equations described herein can be used to iteratively determine pressure, or a simplified model can be used, such as assuming laminar flow.

Figure 10:
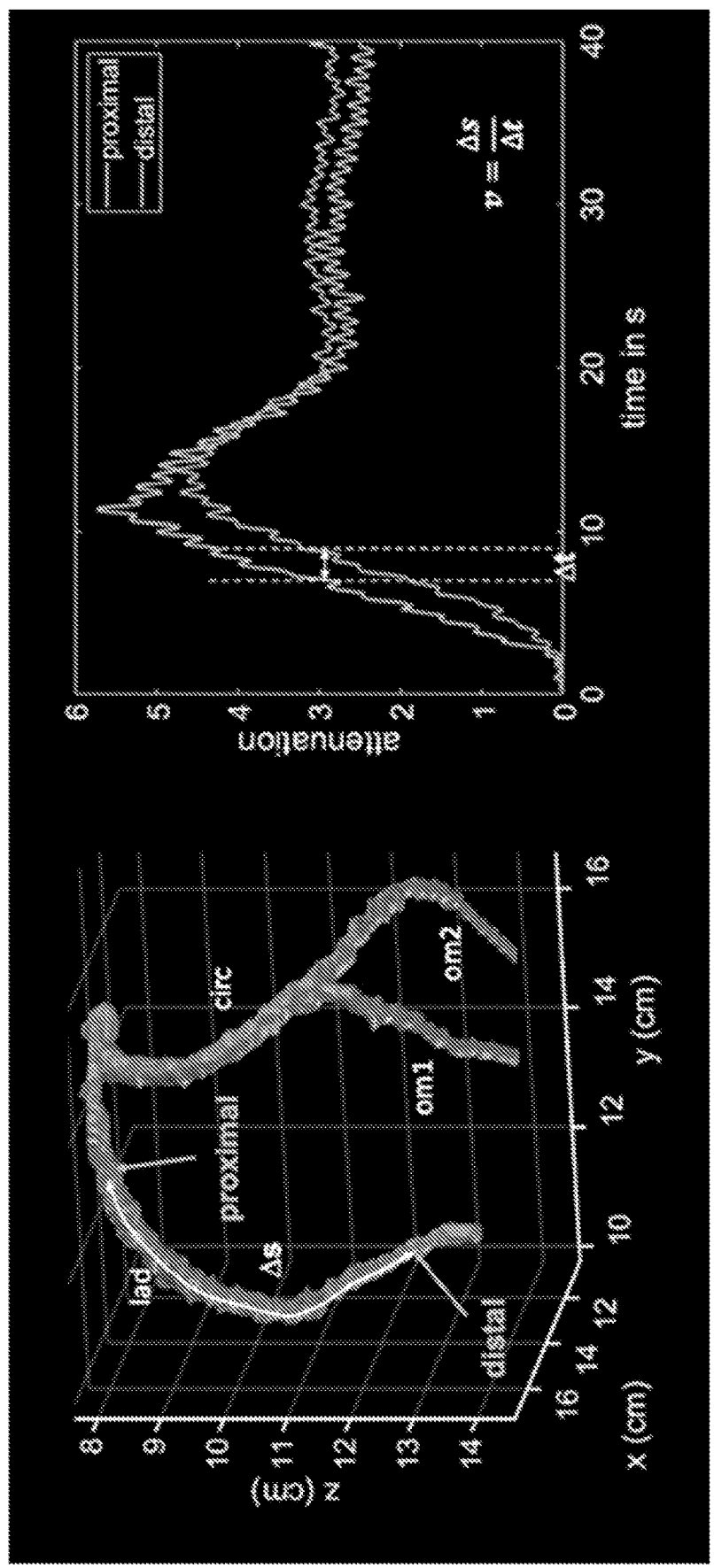
FIG. 10 is a display of a cardiac image and correlated time curves for two positions along a left anterior descending (LAD) generated in accordance with the present disclosure.

As one example, the report may be formed as a map that is displayed. Representative calculations and maps are illustrated in FIG. 10. In this non-limiting example, the averaging kernel was typically chosen to be approximately 0.1 to 1 second. Representative curves for two positions along the left anterior descending (LAD) are shown in FIG. 10. The flow analysis determines the delay in the arrival of contrast for more distal positions along the branch. A method for reliably determining the time shift provides a Δt. Velocity is given by the distance Δs along the centerline divided by Δt.

Figure 11:
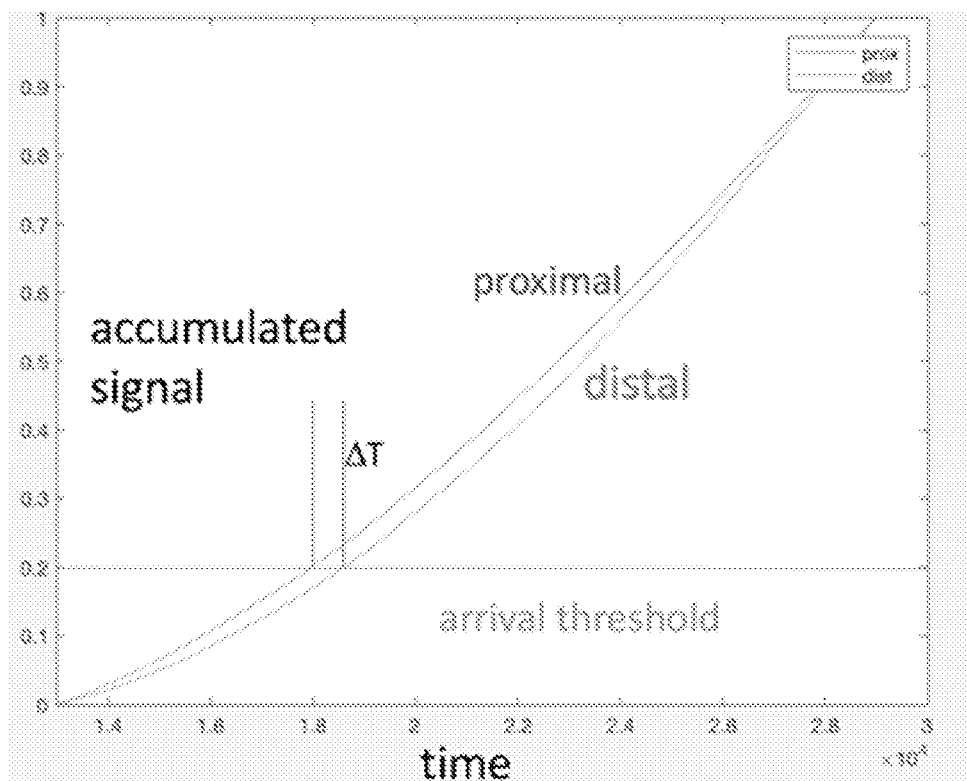
FIG. 11 is a graph of time shift estimated from proximal to distal positions for an arrival threshold of 0.2.

This non-limiting example of a calculation method was used to calculate the accumulated signal for two separated points along a vessel and then to determine the delay associated with crossing a certain percentage of the accumulated signal at these points. In particular, FIG. 11 shows the accumulated signal for two widely separated points along the LAD, illustrating a time shift estimated from proximal to distal positions for an arrival threshold of 20%.

Figure 12:
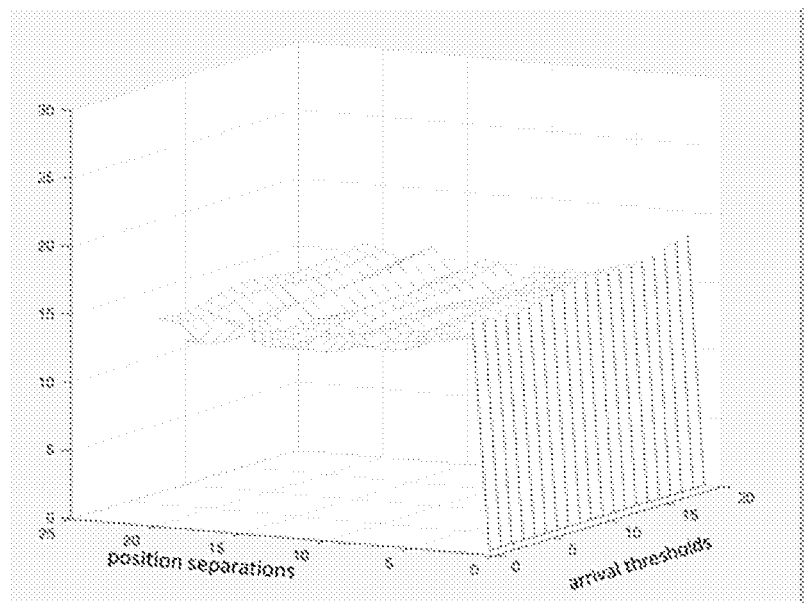
FIG. 12 is a mesh plot of estimated velocity calculated with different arrival time thresholds and position separations along the vessels. Velocity estimates using 20 vessel positions and 20 arrival thresholds between 0.2 and 0.4 are shown.

For a given arrival threshold a Δt is determined for the velocity calculation. The use of the integrated signal curve is less subject to noise than using a raw signal curve threshold. Since the arrival threshold may be varied, it is important to examine the stability of the solution for various choices of arrival threshold. It is also important to look at the stability of the solution for various separations of the points along the vessel. For this purpose, mesh plots of estimated velocity were made for a two-dimensional array of velocities calculated with different arrival time thresholds and position separations along the vessels. Such a plot is shown in FIG. 12, with velocity estimates using 20 vessel positions and 20 arrival thresholds between 20% and 40%.

Figure 13:
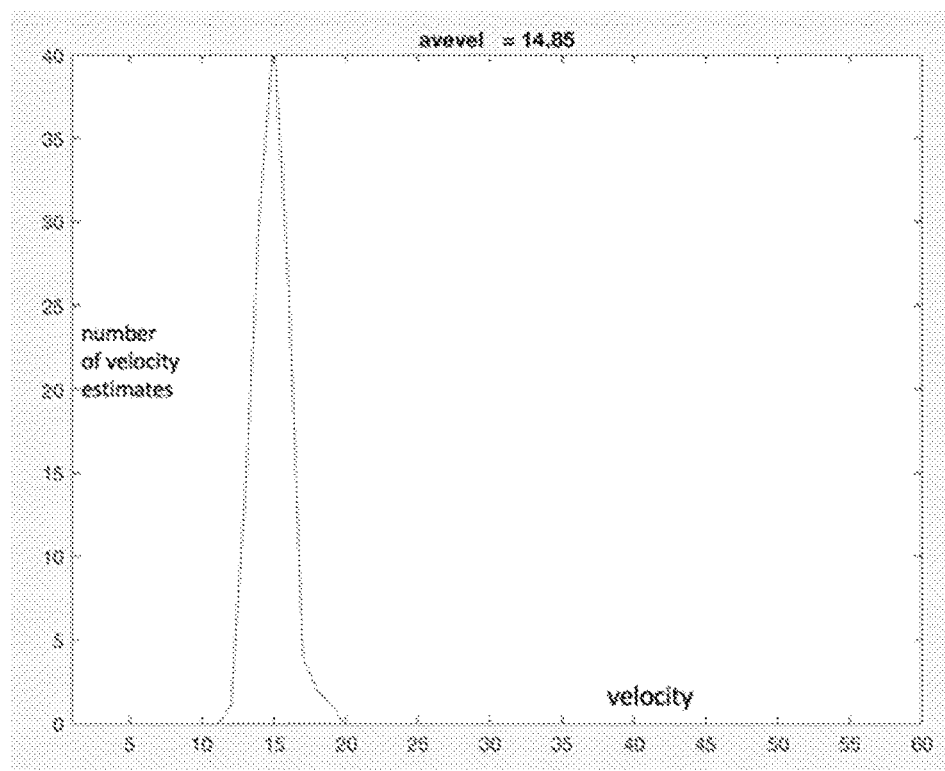
FIG. 13 is a histogram of velocity estimates created using the mesh plot of FIG. 11.

The velocities displayed in this mesh plot are used to form a histogram, and the LAD velocity estimate was taken to be the average velocity in this histogram as shown in FIG. 13. Cross sectional area determinations are made at each point along each centerline. Flows are calculated as the product of the velocity and the average area within each segment. Flow consistency may be checked at each bifurcation.

If it is desired to determine a time shift between two adjacent positions on the vessel centerline separated, for example, by 0.5 mm, assuming a hyperemic velocity of 500 mm/sec, the time shift would be 1 msec. Using the HYPR reconstruction, ~1000 projections are acquired in a fraction of 1 second, so the time separation associated with adjacent positions is readily accommodated. Using the systems and methods provided herein, it is possible to generate velocity estimates using pairs of positions that have larger separation. However, to obtain statistically sound velocity estimates, in some embodiments, the velocity estimates over a range of position pairs are averaged.

In some configurations, local velocity calculations are conducted to generate local velocity maps. In some configurations, for each point along the vasculature or centerlines, time-of-arrival (TOA) is calculated. Other time points may also be used, such as time-to-peak, mean-transit-time, and the like. For example, this can be done based on: a) the time-attenuation curves, by finding the time where signal exceeds predefined threshold or where signal reaches maximum; b) the cumulative time-attenuation curves, by finding the time where signal exceeds a predefined threshold or percentage of maximum; or c) optical tracking or similar techniques based on the 4D reconstruction.

In some configurations, local velocities can be estimated by minimizing a cost function based on the difference between the measured TOA values for each point along the vessel and the TOA values calculated based on the currently estimated local velocities.

Alternatively, in some configurations, local velocities can be calculated by determining per segment flows and dividing by the local cross-sectional area of the vessel.

In some other configurations, pressure/FFR calculations can be made. In some configurations, pressure differences can be calculated based on Navier-Stokes equations. Alternatively, other equations may be used including, but not limited to, a Poisson-equation and an extended Bernoulli equation (e.g., that provides an approximation for the turbulent flow based on the local area and finds use for improved accuracy near stenosis), $$\Delta p = 4v^2\left(1 - \frac{A}{A_{out}}\right)^2; \qquad (5)$$

wherein A is the cross-sectional area in the stenosis, and $A_{out}$ is the cross-sectional area of the output (see e.g., Garcia et al., Circulation, 101:765-771 (2000), herein incorporated by reference in its entirety). In some configurations, Navier-Stokes equations for incompressible fluids with uniform density can be used, even with a simplification such that velocity is assumed constant over time and no external forces, such as gravity, are considered:

$$\nabla p = \rho[v\Delta u - (u \cdot \nabla)u] \qquad (6)$$

Equation (6), thus, is a variation on equation (3), with the body force, f, removed. Based on assumption of physiological aortic pressure, pressure differences are converted to absolute pressure by calculating the sum along centerlines. A pressure ratio can be calculated by dividing absolute pressure by aortic pressure.

Figure 14:
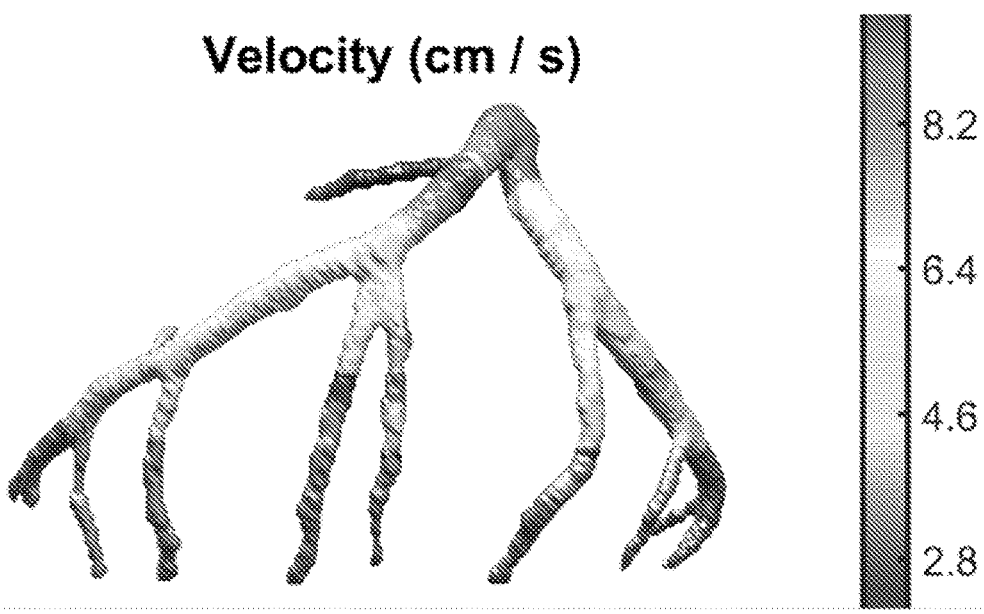
FIG. 14 is a map of local velocity created in accordance with the present disclosure.

Using the systems and methods described above, 3D velocity maps can be generated. When data is acquired at rest and stress, the division of the two velocities provides model-independent values for coronary flow reserve. In some configurations, a velocity map that contains fixed velocity estimates for each branch can be generated by multiplying this value by the average cross sectional value to produce the flow in the branch. Then, imposing the constraint that flow is continuous within a branch, the local velocity can be estimated by dividing the flow by the local area. The result is a local velocity map as shown in FIG. 14.

Figure 15:
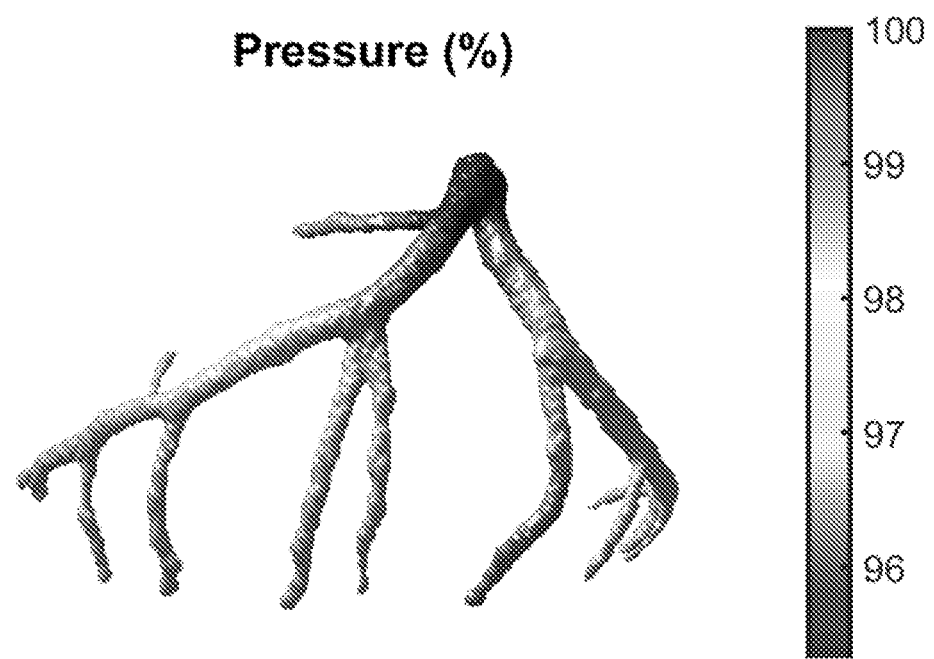
FIG. 15 is a map of relative pressure distribution created in accordance with the present disclosure.

In some configuration, these velocities can be used, along with equation (3), to calculate the local pressure as in FIG. 15. In FIG. 15, measured pressure drops are in mgHg and have been converted to % drops by assuming an aortic pressure of 100 mgHG. Such maps find use to calculate fractional flow reserve estimates.

The generation of the local velocity map can be done in multiple ways. For example, in a first way, the time of arrival can be estimated for each point along the centerlines based on the signal curves. Using numerical optimization techniques, a local velocity map is estimated that is consistent with the estimated time or arrivals. This is done by minimizing a cost function, which calculates time of arrivals based on the velocity map and determines the difference to the estimated arrival times from the signal curves. Instead of the time of arrival other time points can be chosen (e.g. time to peak, mean transit time). Alternatively, one can choose a set of locations on the coronary centerline that are close together, so that the time delay is associated with the local velocity. In a third way, the principle of flow conservation is used. In this case, the total amount of attenuation at each cross-sectional plane of the vessel are measured. Since the flow is conserved, the total amount of contrast medium at each plane is the same and the attenuation is only dependent on the average time each particle requires to travel through one voxel element, which equals to the average inverse velocity. In a fourth way, the average velocity along a coronary segment is used, along with the area information, to determine the flow within the coronary artery. Since flow is conserved, the local velocity is determined by dividing the flow by the local area. In either case a local velocity map such as that shown in FIG. 13 is generated.

Once this is available, in some configurations, the coronary flow reserve can be calculated using velocities derived from rest and stress contrast (e.g., iodine) injections. Additionally, in some configurations, the pressure drops along the coronary vessels can be determined using the Navier-Stokes equations that relate the velocity and velocity gradient to the relative pressure drop according to $\nabla p = \rho[v\Delta u + f - (u \cdot \nabla)u]$, producing maps such as that shown in FIG. 15.

The availability of the velocity maps also serves to provide improved velocity boundary conditions to facilitate various computational fluid dynamic calculations that might be desired, improving the accuracy and speed of the CFD process.

In some configurations, CFD analysis can be used to predict the effects of doing a particular intervention (e.g., administration of a particular therapy). In some configurations, the observed narrowing in a vessel is mathematically corrected and the CFD analysis performed to observe the effects of the intervention. The availability of improved boundary conditions increases the accuracy of this procedure.

Use of Time Resolved Image Series Without HYPR

In some configurations, instead of utilizing the HYPR-based approach described above, time resolved image series provided by modern, rapidly-rotating CT scanners can be utilized. For example, in some configurations, about 4.3 FBP reconstructions can be generated per second using a 400 msec rotation speed resulting in a temporal spacing of 0.230 sec. Assuming hyperemic velocity of 50 cm/sec, blood moves about 11.5 cm, longer than many segments of interest. However, in some configurations, interpolated FBP volumes can be used to reduce the distance. For example, for the above measurements, interpolation by a factor of six calculates average velocity in segments of 2 cm or more. After determining the flow in a branch, conservation of flow is used to generate a local velocity map with pixel resolution. Using a fully-reconstructed FBP volume allows for the coronaries to be segmented for the purpose of generating flow curves without having to perform the LV background subtraction, a process that is can cause variation in estimated velocities.

The present invention has been described in terms of the preferred embodiment, and it should be appreciated that many equivalents, alternatives, variations, and modifications, aside from those expressly stated, are possible and within the scope of the invention. Therefore, the invention should not be limited to a particular described embodiment.

The invention claimed is:

1. A method for determining vascular velocity using non-invasively acquired medical images, the method comprising:
   receiving, at a computer, computed tomography angiography (CTA) data acquired from a subject using a plurality of view angles;
   reconstructing, using the computer, the CTA data into a plurality of images of the subject by:
      producing a composite image using the CTA data corresponding to a set of the plurality of view angles;
      backprojecting each view angle in the CTA data and weighting a value backprojected into at image pixel by an attenuation value of a corresponding pixel in the composite image;
      summing backprojected values for each image pixel to produce a CT image of the subject;
   determining, using the computer, at least one of a flow direction or a velocity of flow within a vessel in the plurality of images of the subject;
   calculating, using the computer and the at least one of flow direction or velocity, a pressure in the vessel; and
   generating, using the computer, a quantitative map of the subject indicating at least one of flow direction, velocity, or pressure in the vessel against an image of the subject including the vessel.

2. The method of claim 1 further comprising calculating, using the computer, a fractional flow reserve (FFR) using the pressure in the vessel.

3. The method of claim 2 further comprising determining, using the computer, a coronary flow reserve.

4. The method of claim 3 wherein the coronary flow reserve is calculated by the FFR from sets of CTA data, wherein one set of CTA data is acquired with the subject at rest and another set of the CTA data is acquired with the subject under stress.

5. The method of claim 1 further comprising generating, using the computer, a local velocity map by applying a flow continuity within a branch of the vessel and a cross-sectional area the vessel measured in the image and displaying the local velocity map against the image.

6. The method of claim 1, wherein the subject has received an intravenous contrast agent prior to acquiring at least some of the CTA data.

7. The method of claim 1, wherein the CTA data comprises 2000 or more CT angiographic images per second.

8. A system for generating quantitative computed tomography (CT) angiographic images, the system comprising:
   a rotatable gantry including a radiation source and a detector coupled thereto, wherein the rotatable gantry is configured to receive a subject to rotate the radiation source and the detector around the subject to acquire a set of projection views forming CTA data of the subject;
   a computer system programmed to receive the CTA data from the detector and generate quantitative CTAs by:
      producing a composite image using the CTA data corresponding to a set of the plurality of view angles;
      backprojecting each view angle in the CTA data and weighting a value backprojected into at image pixel by an attenuation value of a corresponding pixel in the composite image;
      summing backprojected values for each image pixel to produce a CT image of the subject;
   wherein the computer is further programmed to:
      determine at least one of a flow direction or a velocity of flow within a vessel in the plurality of images of the subject;
      calculate, using the at least one of flow direction or velocity, a pressure in the vessel;
      generate a quantitative map of the subject indicating at least one of flow direction, velocity, or pressure in the vessel against an image of the subject including the vessel; and
   a display configured to display the quantitative map of the subject against the image of the subject including the vessel.

9. The system of claim 8 wherein the computer is further programed to determine a fractional flow reserve (FFR) using the pressure in the vessel.

10. The system of claim 9 wherein the computer is further configured to determine a coronary flow reserve.

11. The system of claim 10 wherein the coronary flow reserve is calculated by the FFR from sets of CTA data, and wherein one set of CTA data is acquired with the subject at rest and another set of the CTA data is acquired with the subject under stress.

12. The system of claim 8 wherein the computer s further programmed to generate a local velocity map by applying a flow continuity within a branch of the vessel and a cross-sectional area the vessel measured in the image and displaying the local velocity map against the image.

13. The system of claim 8 wherein the subject has received an intravenous contrast agent prior to acquiring at least some of the CTA data.

14. The system of claim 8 wherein the CTA data comprises 2000 or more CT angiographic images per second.

* * * * *